(12) United States Patent
Jaracz et al.

(10) Patent No.: US 10,053,406 B2
(45) Date of Patent: Aug. 21, 2018

(54) SYNTHESIS OF HONOKIOL

(71) Applicants: Colgate-Palmolive Company, New York, NY (US); The Trustees of the University of Pennsylvania, Philadelphia, PA (US)

(72) Inventors: Stanislav Jaracz, Somerset, NJ (US); Marisa Kozlowski, Wynnewood, PA (US); Young Eun Lee, Elkins Park, PA (US); Sun Min Kim, Philadelphia, PA (US)

(73) Assignees: COLGATE-PALMOLIVE COMPANY, New York, NY (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/331,640

(22) Filed: Oct. 21, 2016

(65) Prior Publication Data

US 2017/0113989 A1    Apr. 27, 2017

Related U.S. Application Data

(60) Provisional application No. 62/316,291, filed on Mar. 31, 2016, provisional application No. 62/245,490, filed on Oct. 23, 2015.

(51) Int. Cl.

| C07C 37/055 | (2006.01) |
|---|---|
| C07C 37/14 | (2006.01) |
| C07C 41/24 | (2006.01) |
| C07C 41/09 | (2006.01) |
| C07C 41/22 | (2006.01) |
| C07C 39/21 | (2006.01) |
| C07C 37/50 | (2006.01) |

(52) U.S. Cl.
CPC .......... *C07C 37/0555* (2013.01); *C07C 37/14* (2013.01); *C07C 37/50* (2013.01); *C07C 39/21* (2013.01); *C07C 41/09* (2013.01); *C07C 41/22* (2013.01); *C07C 41/24* (2013.01)

(58) Field of Classification Search
CPC .......... C07C 39/21; C07C 39/16; C07C 37/14; C07C 41/24; C07C 41/09; C07C 41/22; C07C 37/50; C07C 43/275; C07C 43/29
See application file for complete search history.

(56) References Cited

U.S. PATENT DOCUMENTS

| 3,247,262 | A | * | 4/1966 | Kaeding | ................. C07C 37/11 252/404 |
|---|---|---|---|---|---|
| 5,053,548 | A | | 10/1991 | Tanaka et al. | |
| 8,822,531 | B2 | | 9/2014 | Arbiser | |
| 9,642,834 | B2 | | 5/2017 | Terruzzi et al. | |
| 2006/0210489 | A1 | | 9/2006 | Subramanyam | |
| 2009/0156651 | A1 | | 6/2009 | Mansfield et al. | |

FOREIGN PATENT DOCUMENTS

| WO | WO 1999/000346 | 1/1999 |
|---|---|---|
| WO | WO 2000/040532 | 7/2000 |
| WO | WO 2008/099994 | 8/2008 |
| WO | WO 2017/070568 | 4/2017 |

OTHER PUBLICATIONS

Lee et al. ("Selective Oxidative Homo- and Cross-Coupling of Phenols with Aerobic Catalysts", Journal of the American Chemical Society, May 2014, vol. 136, Issue 19, pp. 6782-6785).*
Omura ("Silver Ion-Mediated Coupling of 4-Bromo-2,6-di-tert-butylcyclohexa-2,5-dienone", J. Org. Chem., Dec. 1998, vol. 63, Issue 26, pp. 10031-10034).*
"2,4-Di-tert-butylphenol," National Center for Biotechnology Information, PubChem Compound Database; CID=7311, https://pubchem.ncbi.nlm.nih.gov/compound/7311 (accessed Nov. 9, 2017).
"2-tert-Butyl-4-methylphenol," National Center for Biotechnology Information, PubChem Compound Database; CID=17004, https://pubchem.ncbi.nlm.nih.gov/compound/17004 (accessed Nov. 9, 2017).
Amblard et al., "Facile Purification of Honokiol and its Antiviral and Cytotoxic Properties," J. Med. Chem., 49(11): 3426-3427 (2006).
Harada et al., "Efficient synthesis of neurotrophic honokiol using Suzuki-Miyaura reactions," Tetrahedron Letters, 55(43): 6001-6003 (2014).
International Search Report for International Application No. PCT/US2016/058258, dated Feb. 23, 2017, 3 pages.
Reddy et al., "A short and efficient synthesis of honokiol via Claisen rearrangement," Tetrahedron Letters, 55(5): 1049-1051 (2014).
Srinivas et al., "Concise total synthesis of honokiol via Kumada cross coupling," Tetrahedron Letters, 55(31): 4295-4297 (2014).

* cited by examiner

*Primary Examiner* — Rosalynd A Keys
(74) *Attorney, Agent, or Firm* — Hoxie & Associates LLC

(57) ABSTRACT

Disclosed herein are improved methods for the synthesis of honokiol, as well as methods for the synthesis of 3,3'-di-tert-butyl-5,5'-dimethyl-[1,1'-biphenyl]-2,4'-diol, 3',5-dimethyl-[1,1'-biphenyl]-2,4'-diol, and 2,4'-dimethoxy-3',5-dimethyl-1,1'-biphenyl, 3,3',5,5'-tetra-tert-butyl-[1,1'-biphenyl]-2,4'-diol, and certain tetrasubstituted bisphenols, and uses therefor.

17 Claims, No Drawings

SYNTHESIS OF HONOKIOL

CROSS REFERENCE TO RELATED APPLICATIONS

This application claims priority to and the benefit of U.S. Provisional Applications 62/245,490, filed on Oct. 23, 2015, and 62/316,291, filed on Mar. 31, 2016, the contents of each of which are incorporated herein by reference in their entireties.

BACKGROUND

Extracts from the bark of the *Magnolia* species, e.g., *Magnolia grandiflora* and *Magnolia officinalis* (Family Magnoliacee), have long been known to possess desirable medicinal and therapeutic properties. Extracts from *Magnolia* bark have been shown to have anti-anxiety, anti-inflammatory, anti-microbial, anti-oxidant, anti-platelet, and neurotrophic properties. A variety of traditional Japanese and Chinese herbal medicines are derived from *Magnolia* species and have long been used to treat anxiety and neurotic disorders. Such herbal formulas include Houpu Tang, Xiao Zhengai Tang, Ping Wei San and Shenmi Tang from China, and Hange-koboku-to and Sai-boku-to from Japan. These formulas are traditionally prepared from the bark of such species as *Magnolia officinalis* and *Magnolia obovata*.

The two major active principles identified in *Magnolia* bark extracts are magnolol and honokiol, which are positional isomers. Honokiol is 3'5-diallyl-2,4'-biphenyldiol (CAS [35354-74-6]) and magnolol is 5,5'-diallyl-2,2'-biphenyldiol (CAS [528-43-8]), as shown below:

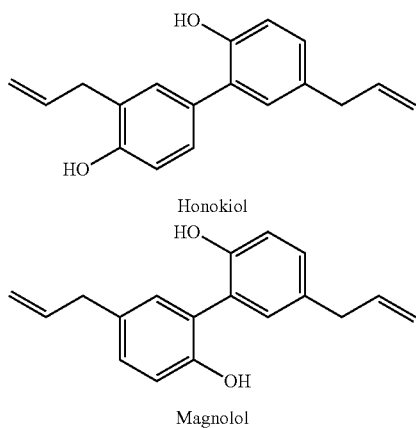

In recent research, these compounds have been purified from extracts and shown to have potent medicinal effects, including anti-proliferative, anti-inflammatory, anti-bacterial, anti-anxiety, chondroprotectieve, neurotrophic and neuroprotective effects. Honokiol, in particular, has been extensively studied as a potential treatment for cancer, heart disease, multiple sclerosis, arthritis and osteoporosis. Honokiol has also found use in consumer products such as toothpastes and mouthwashes, anti-aging creams and as a nutritional supplement. Research has shown that honokiol is a potent promoter of neurite growth and can increase the survival and development of neurons in primary cultures. Honokiol is also a potent anti-proliferative agent against SVR cells in culture, and can selectively inhibit the growth of primary human endothelial cells compared to fibroblasts.

In vivo, honokiol has been shown to be highly effective against angiosarcoma in nude mice, showing both inhibition of angiogenesis and promotion of tumour apoptosis. Indeed, honokiol is being evaluated as an alternative cancer treatments that lacks the side effects of traditional chemotherapy agents.

In addition to honokiol's use as a potential therapeutic agent, honokiol is also in demand as a precursor to derivatives of honokiol which may also have potent biological or therapeutic properties. For example, both dihydrohonokiol and tetrahydrohonokiol are minor components of natural *Magnolia* extract which also display potent pharmaceutical properties. These compounds can be prepared synthetically by the single or double-reduction of the allyl groups of honokiol, respectively. For example, the following two isomeric dihydrohonokiols have been shown to have potent anxiolytic properties in animals:

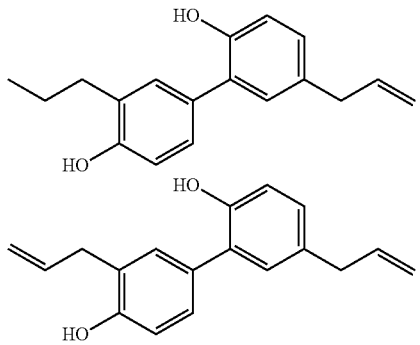

Other honokiol derivatives being evaluated for biological activity include products in which one or both double bonds are converted to cyclopropane rings, epoxide rings, thirane rings or aziridine rings, or compounds in which one or both hydroxy groups are converted to alkyl ethers, trifluoromethyl ethers, alkyl phosphate esters or dichloroacetate esters. For example, honokiol diepoxide has been reported to have potent anti-proliferative effects and to be a potential treatment for cancer:

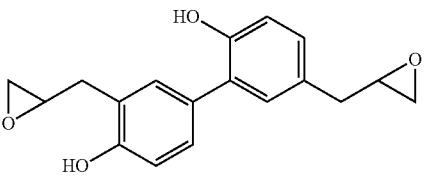 [SMILES: Oc1ccc(-c2cc(CC3CO3)ccc2O)cc1CC1CO1]

Like other natural products, the mass production of honokiol for use in the manufacture of pharmaceutical and consumer products, either directly as an intermediate, would not be cost-effective if based on extraction from natural sources. In addition, extraction from a natural source entails the very high risk that undesirable closely related chemical compounds will be present as impurities in the final product. Instead, commercial viability of honokiol-based products requires an efficient, low-cost, high-yield method of chemical synthesis. However, this goal is also difficult to achieve due to the formation of isomeric compounds that are difficult to separate from the desired compound, honokiol. For example, common synthetic methods produce, in addition to honokiol, the isomeric and difficult-to-separate by-product, isohonokiol:

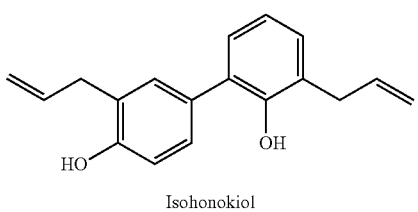 [SMILES: C=CCc1cc(-c2cccc(CC=C)c2O)ccc1O]

Isohonokiol

Many published synthetic methods include other drawbacks, such as costly purification procedures, expensive starting materials, expensive chemical reagents, low overall yields, long reaction times, and toxic metal residues that are difficult to eliminate from the final product.

For example, Reddy et al., Tetrahedron Letters 55 (2014) 1049-1051, discloses a 6-step synthetic method starting from cyclohexane-1,4-dione monoethylene ketal that yields a 2:3 mixture of honokiol and isohonokiol, which are very difficult to separate positional isomers (12% overall yield of honokiol). In addition, the starting material is relatively expensive (greater than $1000/kg). Srinivas, et al., Tetrahedron Letters 55 (2014) 4295-4297, discloses a six-step method starting from 2-bromoanisole involving two palladium catalysed aryl coupling steps that produces honokiol in about 68% overall yield. Palladium catalysed reactions are undesirable because of the very high cost of palladium reagents (e.g., greater than $50,000/kg) and the difficulty of removing palladium impurities from the final product. Harada, et al., Tetrahedron Letters 55 (2014) 6001-6003, report a similar six-step method employing two palladium catalysed coupling steps and starting from 4-hydroxybenzeneboronic acid. The latter compound is both expensive (greater than $4000/kg) and prone to stability issues (which affects the efficiency of the reaction, the purification of intermediates and the storage of starting material). In addition, the use of two steps catalysed by expensive palladium reagents further makes the Harada method poorly suited to commercial use.

There is thus a need for an improved synthetic method for the production of honokiol which is high-yielding, efficient and cost-effective.

BRIEF SUMMARY

The present disclosure provides new, highly efficient methods for the synthesis of honokiol. The methods share the use of a novel, highly efficient metal-catalysed cross-coupling reaction to create the biphenyl core. Both methods are applicable to industrial-scale production in support of the cost-effective production of pharmaceutical and/or consumer products containing honokiol.

In a first aspect, the present disclosure provide Method 1, a method of making honokiol. Method 1 requires five steps and utilizes low-cost starting materials and reagents, and gives high yields of efficiently purified product. In a related embodiment, the present disclosure also provides Method 2, a method of preparing the novel intermediate 3,3'-di-tert-butyl-5,5'-dimethyl-[1,1'-biphenyl]-2,4'-diol.

In a second aspect, the present disclosure provides Method 3, a method of making honokiol. Method 3 requires six steps, and also uses low-cost starting materials and reagents, and give high yields of efficiently purified product. Method 2 uses the final three steps of the Harada procedure (Tetrahedron Letters 55 (2014) 6001-6003), but overcomes the most serious drawbacks by substituting a new three-step sequence to the bis-anisole intermediate. In addition, improved conditions for the final three steps of the Harada procedure are provided. In a related embodiment, the present disclosure also provides Method 4, a method of preparing the intermediate 3,3',5,5'-tetra-tert-butyl-5,5'-[1,1'-biphenyl]-2,4'-diol.

The present disclosure also provides new, useful chemical intermediates, e.g. 3,3'-di-tert-butyl-5,5'-dimethyl-[1,1'-biphenyl]-2,4'-diol, 3',5-dimethyl-[1,1'-biphenyl]-2,4'-diol, and 2,4'-dimethoxy-3',5-dimethyl-1,1'-biphenyl, as well as highly efficient methods for their synthesis and methods for their use in the synthesis of honokiol.

The present disclosure provides a method (Method 1) of making honokiol comprising the reaction of 2-tert-butyl-6-methylphenol with 2-tert-butyl-4-methylphenol to yield 3,3'-di-tert-butyl-5,5'-dimethyl-[1,1'-biphenyl]-2,4'-diol (Compound I):

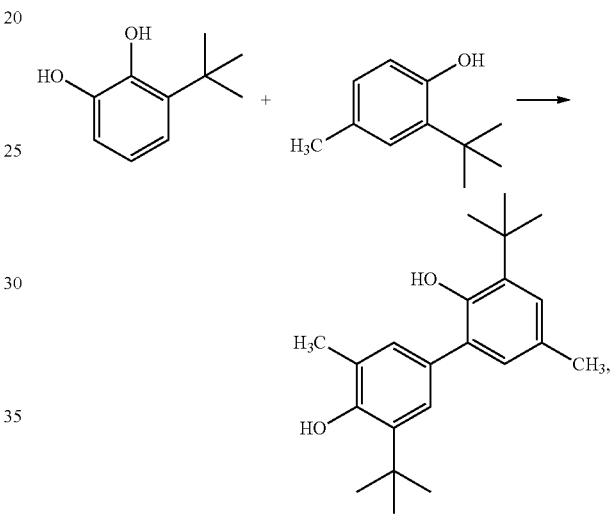

and further comprising the isolation of honokiol. In particular embodiments, the present disclosure provides:

1.1 Method 1, wherein the reaction comprises the use of a metal catalyst (e.g., a chromium, copper, iron, manganese, ruthenium or vanadium catalyst).

1.2 Method 1.1, wherein the metal catalyst comprises the metal atom in complex with an acetylacetonate scaffold or an amine or imine scaffold, e.g., a Salan or Salen scaffold.

1.3 Method 1.2, wherein the metal catalyst comprises a chromium-Salen complex.

1.4 Method 1.2, wherein the metal catalyst is Cr-Salen-Cy or manganese acetylacetonate.

1.5 Method 1, or any of 1.1 et seq., wherein the reaction further comprises an oxidant.

1.6 Method 1, or any of 1.1 et seq., wherein the oxidant is oxygen.

1.7 Method 1, or any of 1.1 et seq., wherein the oxidant is silver (I) acetate or di(tert-butyl) peroxide.

1.8 Method 1, or any of 1.1 et seq., wherein the solvent is toluene.

1.9 Method 1, or any of 1.1 et seq., wherein the temperature of the reaction is from 70° C. to 140° C., e.g., from 80° C. to 90° C.

1.10 Method 1, or any of 1.1 et seq., further comprising, in any order, one or more of the following steps:

a. dealkylation of the t-butyl groups of Compound I,
b. alkylation of the phenolic oxygens of Compound I or II,
c. benzylic halogenation of the methyl groups of Compound I, II or III,
d. substitution of the halogens of Compound IV or the halo derivative of Compound I, II or III with a vinyl reagent (e.g., vinyl organometallic reagent), and
e. dealkylation of the alkyl ether groups of Compound V or the allyl derivatives of Compound I, II, III.

1.11 Method 1, or any of 1.1 et seq., further comprising the de-alkylation (e.g., retro-Friedel Crafts alkylation) of Compound I to yield Compound II:

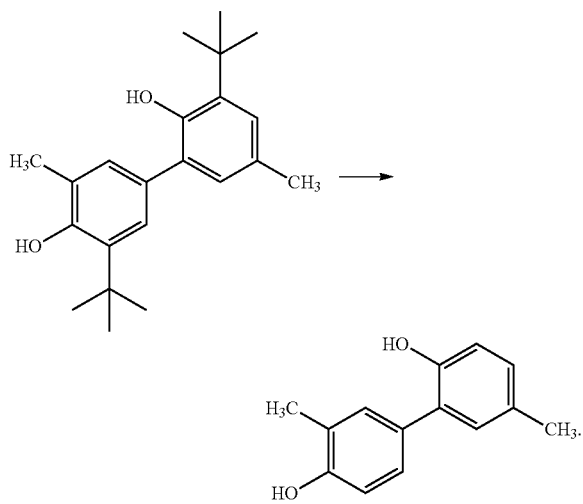

1.12 Method 1, or any of 1.1 et seq., wherein the reaction comprises the use of a Lewis acid catalyst (e.g., a metal halide catalyst).
1.13 Method 1.12, wherein the Lewis acid catalyst is aluminum chloride.
1.14 Method 1, or any of 1.1 et seq., wherein the cross-coupling reaction and the dealkylation reaction occurs in the same reaction vessel without isolation of the intermediate Compound I.
1.15 Method 1, or any of 1.1 et seq., further comprising the methylation of Compound II to yield Compound III:

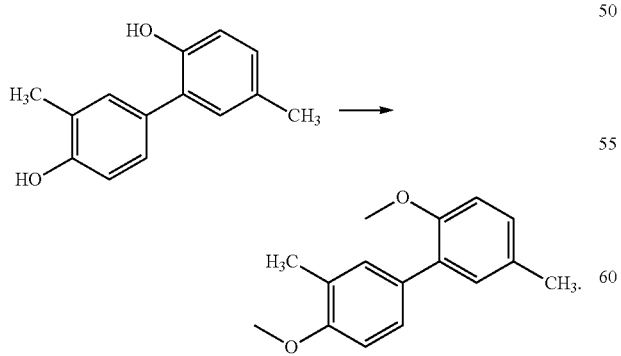

1.16 Method 1, or any of 1.1 et seq., wherein the methylation comprises the use of methyl iodide or methyl sulfate and a suitable base (e.g., potassium carbonate).

1.17 Method 1, or any of 1.1 et seq., wherein the cross-coupling reaction, the dealkylation reaction, and the methylation reaction occurs in the same reaction vessel without isolation of the intermediate Compounds I and II.
1.18 Method 1, or any of 1.1 et seq., further comprising the benzylic halogenation of Compound III to yield Compound IV, wherein X is bromine, chlorine or iodine:

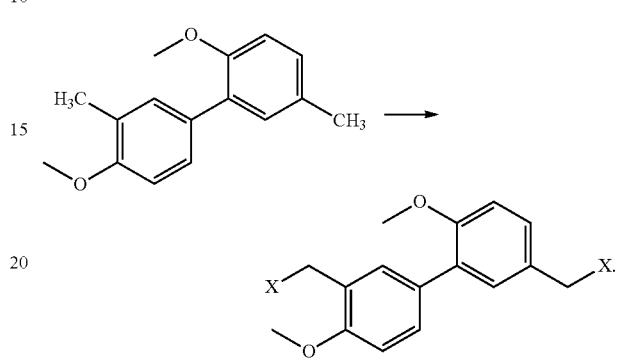

1.19 Method 1, or any of 1.1 et seq., wherein X is bromine
1.20 Method 1, or any of 1.1 et seq., wherein the reaction comprises the use of N-bromosuccinimide with a radical initiator (e.g., azobisisobutyronitrile).
1.21 Method 1, or any of 1.1 et seq., further comprising the coupling of a vinylmetallic agent with Compound IV to yield di-allyl compound V:

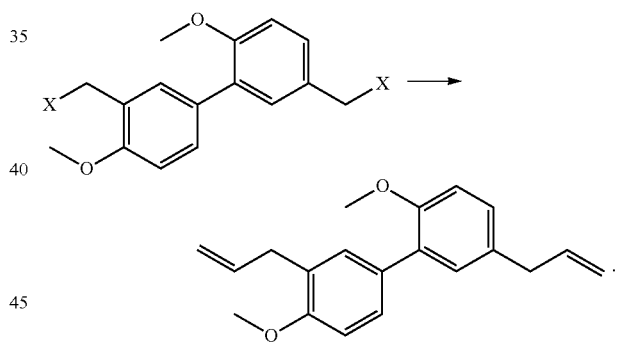

1.22 Method 1, or any of 1.1 et seq., wherein the vinylmetallic agent is selected from the group consisting of: vinylmagnesium bromide, vinylmagnesium chloride, vinylmagnesium iodide, vinyllithium, and divinylcopper lithium.
1.23 Method 1, or any of 1.1 et seq., wherein the reaction further comprises a copper (I) catalyst (e.g., copper(I) iodide, copper(I) bromide, or copper(I) chloride).
1.24 Method 1, or any of 1.1 et seq., further comprising the demethylation of Compound V to yield honokiol:

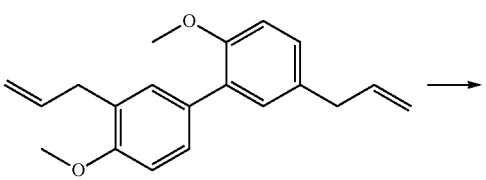

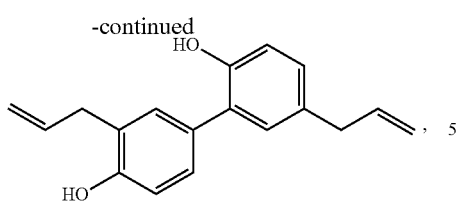

and the isolation of the honokiol from the reaction mixture.

1.25 Method 1, or any of 1.1 et seq., wherein the reaction comprises the use of boron tribromide, optionally in dichloromethane, dichloroethane or toluene solvent.

1.26 Method 1, or any of 1.1 et seq., wherein the reaction comprises the use of boron-tribromide-dimethyl sulfide complex.

In another aspect, the present disclosure provides a method (Method 2) of making 3,3'-di-tert-butyl-5,5'-dimethyl-[1,1'-biphenyl]-2,4'-diol (Compound I) comprising the reaction of 2-tert-butyl-6-methylphenol with 2-tert-butyl-4-methylphenol:

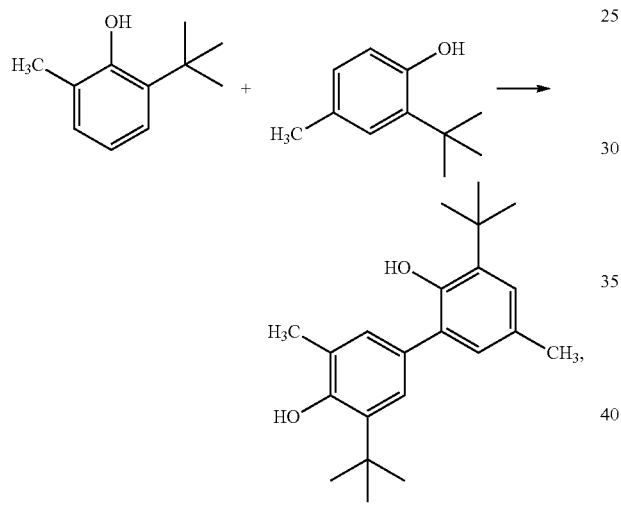

and optionally further comprising the isolation of Compound I from the reaction mixture. In particular embodiments, the present disclosure provides:

2.1 Method 2, wherein the reaction comprises the use of a metal catalyst (e.g., a chromium, copper, iron, manganese, ruthenium or vanadium catalyst).

2.2 Method 2 or 2.1, wherein the metal catalyst comprises the metal atom in complex with an acetylacetonate scaffold, or an amine or imine scaffold, e.g., a Salan or Salen scaffold.

2.3 Method 2.2, wherein the metal catalyst comprises a chromium-Salen complex.

2.4 Method 2.2, wherein the metal catalyst is Cr-Salen-Cy or manganese acetylacetonate.

2.5 Method 2, or any of 2.1 et seq., wherein the reaction further comprises an oxidant.

2.6 Method 2, or any of 2.1 et seq., wherein the oxidant is oxygen.

2.7 Method 2, or any of 2.1 et seq., wherein the oxidant is silver (I) acetate or di(tert-butyl) peroxide.

2.8 Method 2, or any of 2.1 et seq., wherein the solvent is toluene.

2.9 Method 2, or any of 2.1 et seq., wherein the temperature of the reaction is from 70° C. to 140° C., e.g., from 80° C. to 90° C.

In another aspect, the present disclosure also provides:

3.1 Compound I:

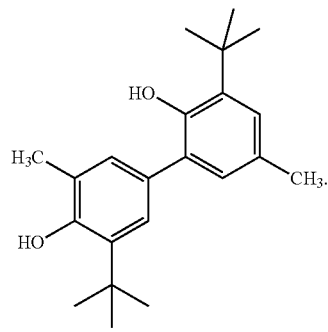 [SMILES: Cc1cc(-c2cc(C)c(O)c(C(C)(C)C)c2)c(O)c(C(C)(C)C)c1]

3.2 Compound II:

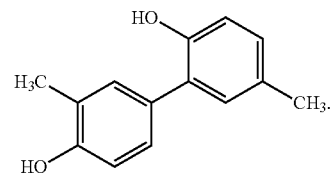 [SMILES: Cc1ccc(O)c(-c2ccc(O)c(C)c2)c1]

3.3 Compound III:

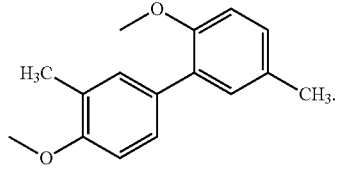 [SMILES: COc1ccc(-c2cc(C)ccc2OC)cc1C]

3.4 Compound IV:

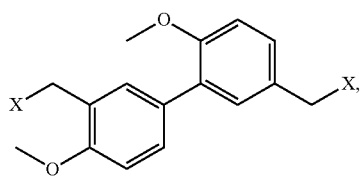

wherein X is selected from bromine, chlorine or iodine (e.g., wherein X is bromine).

3.5 A compound selected from Compound I, Compound II, Compound III or Compound IV, as shown in 3.1-3.4.

3.6 The use any one or more of Compounds I, II, III or IV (e.g., wherein X is bromine chlorine or iodine) in the making of honokiol.

3.7 Any one or more of Compound I, Compound II, Compound III or Compound IV (e.g., wherein X is bromine, chlorine or iodine) for use in the manufacture of a medicament comprising honokiol.

In another aspect, the present disclosure provides a method (Method 3) of making honokiol comprising the reaction of 2,6-di-tert-butyl-6-phenol with 2,4-di-tert-butyl- 4-phenol to yield 3,3',5,5'-tetra-tert-butyl-5,5'-[1,1'-biphenyl]-2,4'-diol (Compound VI):

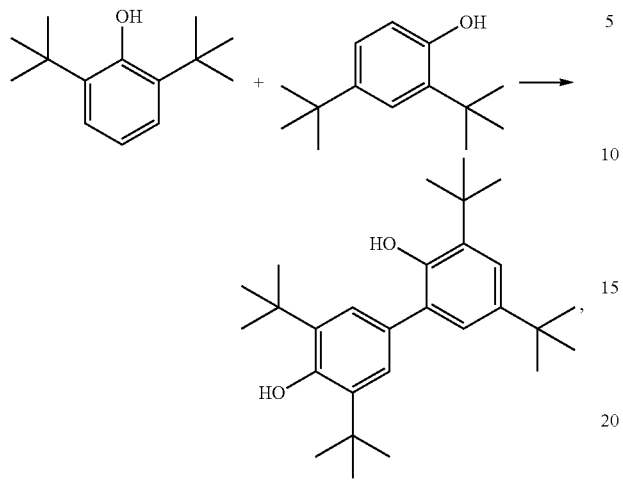

and further comprising the isolation of honokiol. In particular embodiments, the present disclosure provides:

3.1 Method 3, wherein the reaction comprises the use of a metal catalyst (e.g., a chromium, copper, iron, manganese, ruthenium or vanadium catalyst).

3.2 Method 3.1, wherein the metal catalyst comprises the metal atom in complex with an acetylacetonate scaffold or an amine or imine scaffold, e.g., a Salan or Salen scaffold.

3.3 Method 3.2, wherein the metal catalyst comprises a chromium-Salen complex, iron-Salen complex, or ruthenium Salen complex.

3.4 Method 3.2, wherein the metal catalyst is Cr-Salen-Cy, Fe-Salen-Cy or Ru-Salen-H.

3.5 Method 3, or any of 3.1 et seq., wherein the reaction further comprises an oxidant.

3.6 Method 3, or any of 3.1 et seq., wherein the oxidant is oxygen.

3.7 Method 3, or any of 3.1 et seq., wherein the oxidant is silver (I) acetate or di(tert-butyl) peroxide.

3.8 Method 3, or any of 3.1 et seq., wherein the solvent is toluene or chlorobenzene.

3.9 Method 3, or any of 3.1 et seq., wherein the temperature of the reaction is from 70° C. to 140° C., e.g., from 80° C. to 130° C., or about 80° C. or about 130° C.

3.10 Method 3, or any of 3.1 et seq., further comprising, in any order, one or more of the following steps:
 a. dealkylation of the four t-butyl groups of Compound VI,
 b. alkylation of the two phenolic oxygens of Compound VI or VII,
 c. electrophilic aromatic halogenation of the Compound VI, VII or VIII,
 d. substitution of the halogens of Compound IX or the halo derivative of Compound VI, VII or VIII with an allyl reagent (e.g., an allyl organometallic reagent or allyl halide), and
 e. dealkylation of the alkyl ether groups of Compound V or the allyl derivatives of Compound VI, VII, VIII.

3.11 Method 3, or any of 3.1 et seq., further comprising the de-alkylation (e.g., retro-Friedel Crafts alkylation) of Compound VI to yield Compound VII:

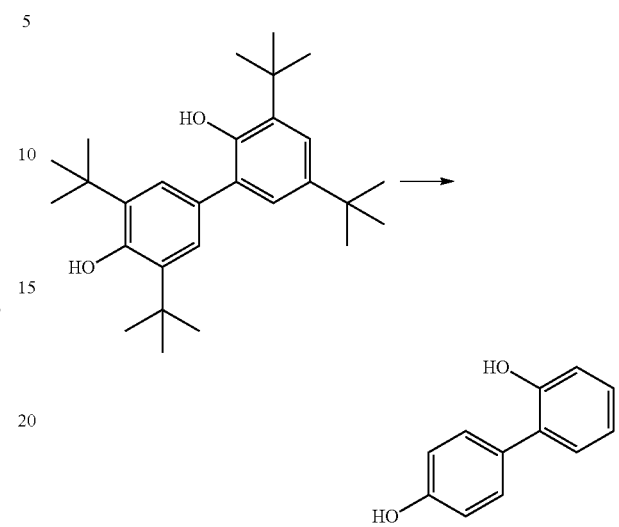

3.12 Method 3, or any of 3.1 et seq., wherein the reaction comprises the use of an acid catalyst, such as a Lewis acid (e.g., a metal halide catalyst) or a Bronsted acid.

3.13 Method 3.12, wherein the Lewis acid catalyst is aluminum chloride.

3.14 Method 3.12, wherein the Bronsted acid is methanesulfonic acid.

3.15 Method 3, or any of 3.1 et seq., wherein the cross-coupling reaction and the dealkylation reaction occurs in the same reaction vessel without isolation of the intermediate Compound VI.

3.16 Method 3, or any of 3.1 et seq., further comprising the methylation of Compound VII to yield Compound VIII:

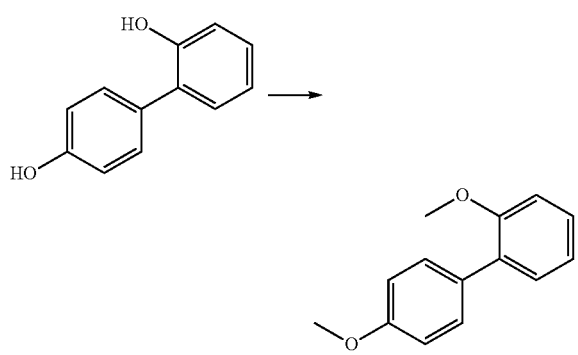

3.17 Method 3, or any of 3.1 et seq., wherein the methylation comprises the use of methyl iodide or methyl sulfate and a suitable base (e.g., potassium carbonate).

3.18 Method 3, or any of 3.1 et seq., wherein the cross-coupling reaction, the dealkylation reaction, and the methylation reaction occurs in the same reaction vessel without isolation of the intermediate Compounds VI and VII.

3.19 Method 3, or any of 3.1 et seq., further comprising the electrophilic aromatic halogenation of Compound VIII to yield Compound IX, wherein X is bromine, chlorine or iodine:

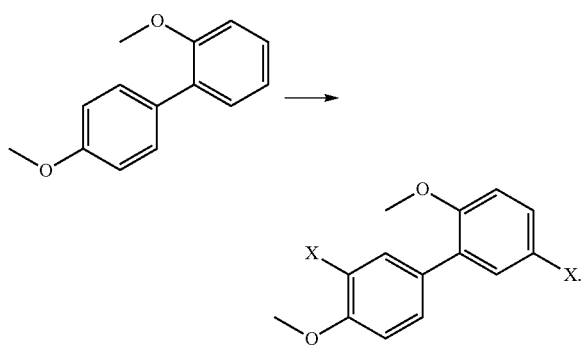

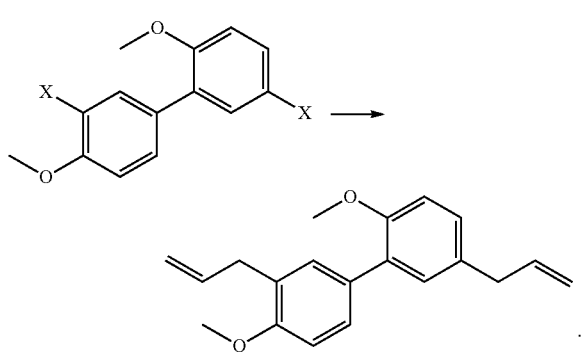

3.20 Method 3, or any of 3.1 et seq., wherein X is bromine
3.21 Method 3, or any of 3.1 et seq., wherein the reaction comprises the use of bromine and a radical initiator (e.g., hydrogen peroxide, t-butyl peroxide, or AIBN).
3.22 Method 3, or any of 3.1 et seq., further comprising the coupling of a allyl reagent (e.g., an allyl organometallic agent) or an allyl halide (e.g., allyl bromide) with Compound IX to yield di-allyl compound V:

3.23 Method 3, or any of 3.1 et seq., wherein the coupling of the allyl reagent with Compound IX comprises the steps of: (1) converting the aromatic halides of Compound IX into metallohalides (e.g., MgBr, MgCl, MgI) and (2) substituting the allyl group of an allyl halide (e.g., allyl bromide) for the metallohalide via palladium catalysed coupling (e.g., with a palladium(0) catalyst).
3.24 Method 3.23, wherein step (1) comprises the use of magnesium and catalytic iodine, in a suitable solvent (e.g, THF)
3.25 Method 3.23 or 3.24, wherein step (2) comprises the use of tetrakis(triphenylphosphine)palladium(0).
Method 3, or any of 3.1 et seq., wherein the coupling of the allyl reagent with Compound IX comprises the steps of: (1) reaction with an allyl organometallic reagent (e.g., allyl lithium, allyl magnesium chloride, allyl magnesium iodide or allyl magnesium bromide), in the presence of a palladium catalyst (e.g., palladium acetate), optionally further comprising a ligand (e.g., a phosphine ligand, such as X-Phos, or BrettPhos), and optionally (2) further reaction with an allyl halide reagent (e.g., allyl chloride, allyl bromide or allyl iodide).
3.26 Method 3.25, wherein step (1) of the coupling comprises the use of allyl magnesium chloride or allyl magnesium bromide.
3.27 Method 3.25 or 3.26, wherein step (2) of the coupling comprises the use of palladium acetate and X-Phos ligand.
3.28 Method 3.27, further comprising further reaction with the allyl chloride or allyl bromide.
3.29 Method 3, or any of 3.1 et seq., further comprising the demethylation of Compound V to yield honokiol:

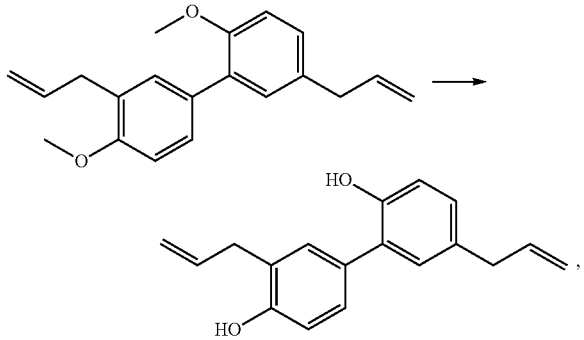

and the isolation of the honokiol from the reaction mixture.
3.30 Method 3, or any of 3.1 et seq., wherein the reaction comprises the use of boron tribromide, optionally in dichloromethane, dichloroethane or toluene solvent.
3.31 Method 3, or any of 3.1 et seq., wherein the reaction comprises the use of boron-tribromide-dimethyl sulfide complex, optionally in DCE solvent.

In another aspect, the present disclosure provides a method (Method 4) of making 3,3',5,5'-tetra-tert-butyl-5,5'-[1,1'-biphenyl]-2,4'-diol (Compound VI), comprising the reaction of 2,6-di-tert-butyl-6-phenol with 2,4-di-tert-butyl-4-phenol:

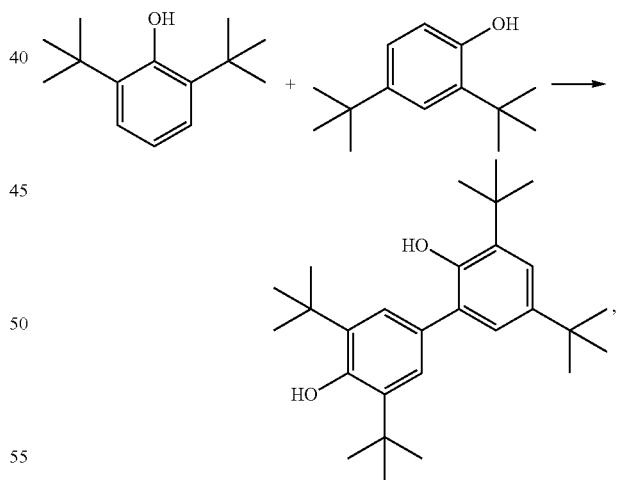

and optionally further comprising the isolation of Compound VI from the reaction mixture. In particular embodiments, the present disclosure provides:
4.1 Method 4, wherein the reaction comprises the use of a metal catalyst (e.g., a chromium, copper, iron, manganese, ruthenium or vanadium catalyst).
4.2 Method 4.1, wherein the metal catalyst comprises the metal atom in complex with an acetylacetonate scaffold or an amine or imine scaffold, e.g., a Salan or Salen scaffold.

4.3 Method 4.2, wherein the metal catalyst comprises a chromium-Salen complex, iron-Salan complex, or ruthenium Salen complex.
4.4 Method 4.2, wherein the metal catalyst is Cr-Salen-Cy, Fe-Salen-Cy or Ru-Salen-H.
4.5 Method 4, or any of 4.1 et seq., wherein the reaction further comprises an oxidant.
4.6 Method 4, or any of 4.1 et seq., wherein the oxidant is oxygen.
4.7 Method 4, or any of 4.1 et seq., wherein the oxidant is silver (I) acetate or di(tert-butyl) peroxide.
4.8 Method 4, or any of 4.1 et seq., wherein the solvent is toluene or chlorobenzene.
4.9 Method 4, or any of 4.1 et seq., wherein the temperature of the reaction is from 70° C. to 140° C., e.g., from 80° C. to 130° C., or about 80° C. or about 130° C.

In another aspect, the present disclosure provides a method (Method 5) of making a tetrasubstituted bisphenol (Compound X), comprising the reaction of two disubstituted phenols, wherein the reaction comprises the use of a metal catalyst:

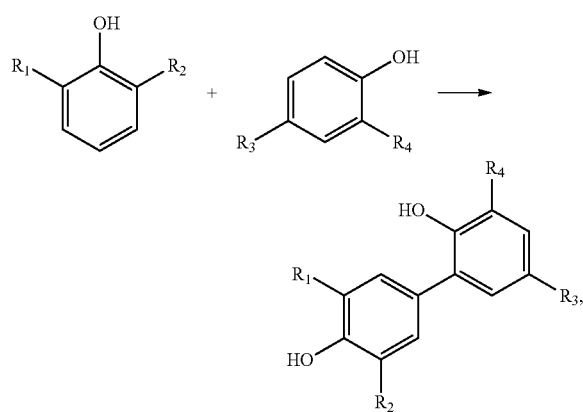

Compound X wherein $R_1$, $R_2$, $R_3$ and $R_4$ are each independently a $C_{1-10}$ alkyl, $C_{1-10}$ alkylene, or $C_{1-10}$ alkynylene, optionally substituted with ether, sulfide, ester, amide, halide, nitrile or amino groups, and wherein the $C_{1-10}$ backbone is optionally straight or branched, and optionally further comprising the isolation of the compound X from the reaction mixture.

In particular embodiments, the present disclosure provides:
5.1 Method 5, wherein $R_1$, $R_2$, $R_3$ and $R_4$ are each independently a $C_{1-10}$ alkyl.
5.2 Method 5.1, wherein $R_1$, $R_2$, $R_3$ and $R_4$ are each independently a $C_{1-4}$ alkyl group, optionally straight or branched (e.g., methyl, ethyl, propyl, isopropyl, butyl, isobutyl, sec-butyl, or t-butyl).
5.3 Method 5, or any of 5.1 et seq., wherein the metal catalyst is selected from a chromium, copper, iron, manganese, ruthenium or vanadium catalyst.
5.4 Method 5.3, wherein the metal catalyst comprises the metal atom in complex with an acetylacetonate scaffold or an amine or imine scaffold, e.g., a Salan or Salen scaffold.
5.5 Method 5.4, wherein the amine or imine scaffold is a Salan or Salen scaffold.
5.6 Method 5.5, wherein the metal catalyst comprises a chromium-Salen complex, iron-Salen complex, manganese-Salen complex, ruthenium-Salen, copper-Salen, cobalt-Salen, vanadium-Salen, chromium-Salan complex, iron-Salan complex, manganese-Salan complex, ruthenium-Salan, copper-Salan, cobalt-Salan, or vanadium-Salan complex.
5.7 Method 5.5, wherein the metal catalyst is Cr-Salen-Cy, Fe-Salan-Cy or Ru-Salen-H, Ru-Salan-H, Co-Salen-H, V-Salan-Cy, or Cr-Salan-Cy.
5.8 Method 5.4, wherein the metal catalyst is manganese acetylacetonate.
5.9 Method 5, or any of 5.1 et seq., wherein the reaction further comprises an oxidant.
5.10 Method 5, or any of 5.1 et seq., wherein the oxidant is selected from oxygen, peroxides, hydroperoxides, peroxy acids, or inorganic oxidizing agents.

In some embodiments, the present disclosure also provides for the use of the method in the synthesis of derivatives of honokiol, such as dihydrohonokiols, tetrahydrohonokiol, mono- and di-epoxides of honokiol, and other derivatives.

DETAILED DESCRIPTION

Each reference cited herein is hereby incorporated by reference in its entirety.

All percentages and ratios used herein are by weight of the oral care composition, unless otherwise specified. All measurements are made at 25° C., unless otherwise specified.

Throughout this description and claims, the disclosure of a certain numerical value (e.g., temperature, weight percent of components, etc.) is meant to denote that value, plus or minus an additional value that would be understood by persons having ordinary skill in the art, depending on the variable and the degree of measurement error typically associated with that value. For example, a given temperature would be understood by a person having ordinary skill in the art to include up to 10% variability, given the instrument used to measure the temperature.

As used herein, "extracting" or "extraction" of a solid or liquid material means contacting the material with an appropriate material, such as a solvent to remove the substance(s) desired to be extracted from the material. Such an extraction may be carried out by conventional means known to one of skill in the art, for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

The present disclosure provides a method (Method 1) of making honokiol comprising the reaction of 2-tert-butyl-6-methylphenol with 2-tert-butyl-4-methylphenol to yield 3,3'-di-tert-butyl-5,5'-dimethyl-[1,1'-biphenyl]-2,4'-diol (Compound I), as shown below:

Compound I

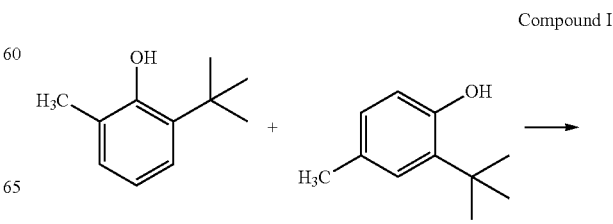

-continued

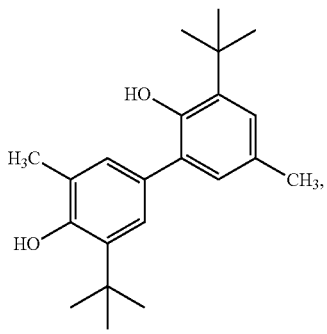

followed by the isolation of Honokiol.

This reaction is an example of a catalytic oxidative phenol cross-coupling between a 2,6-disubstituted phenol and a 2,4-disubstituted phenol. The reaction is difficult because the catalyst must promote the cross-coupling reaction at a significantly faster rate than the two competing homo-coupling reactions.

Suitable catalysts for oxidative phenol cross-coupling reaction (including those of Methods 1-5, 1.1-1.23, 2.1-2.6, 3.1-3.27, 4.1-4.6 and 5.1-5.10) include metal catalyst systems in which the metal can be readily reoxidized by diatomic oxygen, peroxide or other suitable oxidation reagent. Such metals include chromium (Cr), copper (Cu), iron (Fe), manganese (Mn), ruthenium (Ru) and vanadium (V). In selected embodiments, the metal is chromium or manganese. The metal is employed as part of a complex in which the metal is coordinated to an amine or imine scaffold or to acetylacetonate scaffold, for example, a salan (N,N'-ethylenebis(salicylamine)) or salen (N,N'-ethylenebis(salicylimine) scaffold. In some embodiments, the phenyl rings of the salan or salen ligand are substituted with an ortho-alkyl group, e.g., an ortho t-butyl group. In some embodiments, the ethylene bridge of the scaffold is substituted, e.g., 1,2-trans-dialkyl, 1,2-trans-diaryl, or 1,2-trans-fused cycloalkane. In selected embodiments, the scaffold is a Salan-Ph or Salen-Ph (1,2-trans-diphenyl bridge), or Salan-Cy or Salen-Cy (1,2-trans fused cyclohexane bridge). In one embodiment the catalyst complex is selected from Cr-Salen-Cy, Mn-Salen-Ph, or Cu-Salen-Cy. These are relatively inexpensive metal catalysts. For example, the catalyst may be Cr-Salen-Cy, as shown below, which is commercially available for less than $20/kg:

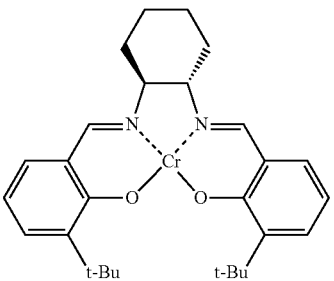

In other embodiments, the catalyst may be manganese (III) acetylacetonate (also known as manganic acetylacetonate, or Mn(acac)$_3$).

The oxidative phenol cross-coupling reaction is carried out in a suitable solvent or mixture of solvents and in the presence of an oxidant. Suitable solvents include dichloroethane (DCE), tetrachloroethane (TCE), carbon tetrachloride, benzene, toluene, trifluoromethylbenzene, chlorobenzene, dichlorobenzene, and other highly nonpolar aliphatic and aromatic solvents, or mixtures thereof. In some embodiments, the solvent is dichloroethane. The mechanism of the cross-coupling reaction involves the conversion of the active metal center (in a higher oxidation state) to an inactive metal center (in a lower oxidation state). For example, if the cross-coupling catalyst is a chromium catalyst, the reaction involves the conversion of the active Cr(IV) species to an inactive Cr(III) species. As a result, the reaction mixture must comprise an oxidant which is capable of reoxidizing the consumed metal center (e.g., Cr(III)) back to its higher oxidation state (e.g., Cr(IV)). The oxidant can be any species capable of performing this oxidation, for example, air, diatomic oxygen ($O_2$), ozone, peroxides (e.g., hydrogen peroxide, di-tert-butyl peroxide), hydroperoxides (e.g., tert-butylhydroperoxide), peroxy acids (e.g., peracetic acid, peroxymonosulfuric acid, meta-chloroperoxybenzoic acid, trifluoroperacetic acid, performic acid), inorganic oxidizing agents (e.g., sodium hypochlorite, sodium chlorite, sodium chlorate, sodium perchlorate, potassium permanganate, manganese dioxide, selenium dioxide, chromate salts, dichromate salts, silver (I) acetate, sodium periodate, sodium bromate, etc.) and other organic oxidizing agents (e.g., iodosobenzene, iodoxybenzoic acid and other hypervalent iodine reagents). In selected embodiments, the oxidant is oxygen.

In some embodiments, Method 1 further comprises, in any order, one or more of the following steps: dealkylation of the t-butyl groups of Compound I, alkylation of the phenolic oxygens of Compound I or II, benzylic halogenation of the methyl groups of Compound I, II or III, substitution of the halogens of Compound IV or the halo derivative of Compound I, II or III with a vinyl reagent (e.g., vinyl organometallic reagent) to yield a mono- or di-allyl compound, dealkylation of the alkyl ether groups of Compound V or the mono- or di-allyl derivatives of Compound I, II, III, and the isolation of Honokiol product.

In a particular embodiment, Method 1 further comprises the following steps in order as shown in the scheme below: the dealkylation of the t-butyl groups of Compound I to yield Compound II, the alkylation of the phenolic oxygens of Compound II to yield Compound III-A, the benzylic halogenation of Compound III-A to yield Compound IV-A, the vinyl substitution of Compound IV-A to yield Compound V-A, and the dealkylation of Compound V-A to yield Honokiol, and isolation thereof. In Compounds III-A, IV-A and V-A, R may be any $C_{1-6}$ alkyl group, including straight-chain, branched and/or substituted, e.g., substituted with one or more $C_{1-6}$ alkyl ethers or substituted with one or more $C_{1-6}$ alkyl or aryl ether or mixed silyl ethers. Examples of such R groups include, but are not limited to, methyl, ethyl, propyl, isopropyl, t-butyl, benzyl, methoxymethyl, benzyloxymethyl, 2-methoxyethoxymethyl, 1-ethoxyethyl, 2-trimethylsilylethyl, trimethylsilyl, triethylsilyl, triisopropylsilyl, t-butyldimethylsilyl, t-butyldiphenylsilyl, diphenylmethylsilyl, di-t-butylmethylsilyl, and the like.

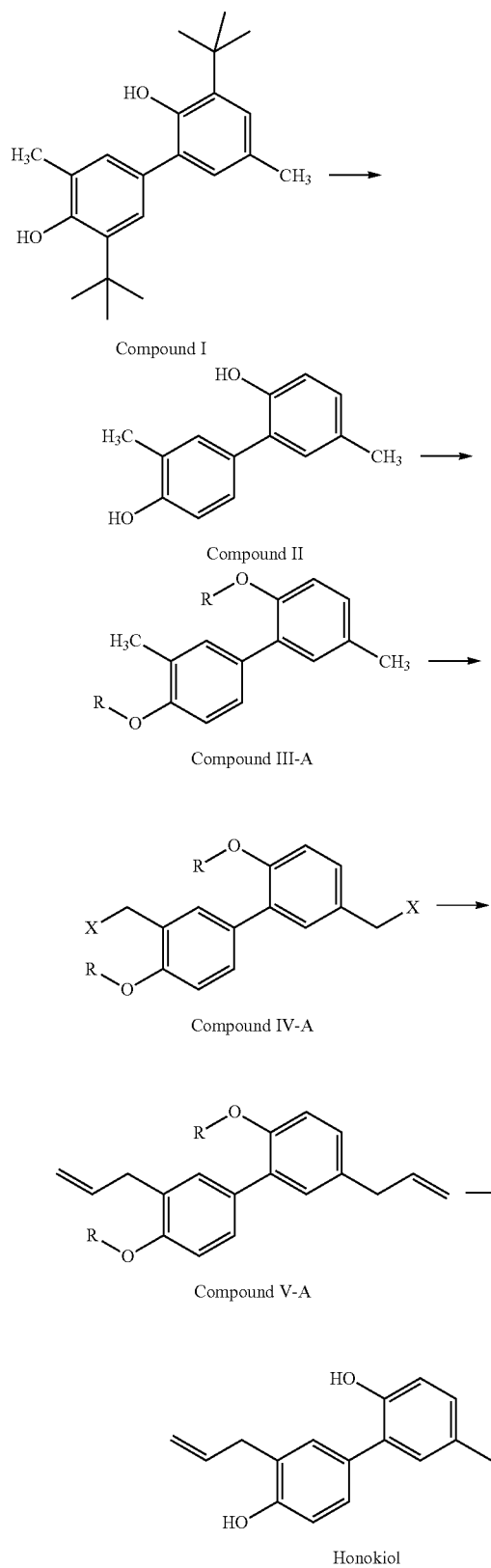

Compound I

Compound II

Compound III-A

Compound IV-A

Compound V-A

Honokiol

In some embodiments, Method 1 further comprises the dealkylation of Compound I to yield Compound II (e.g., a retro Friedel Crafts alkylation):

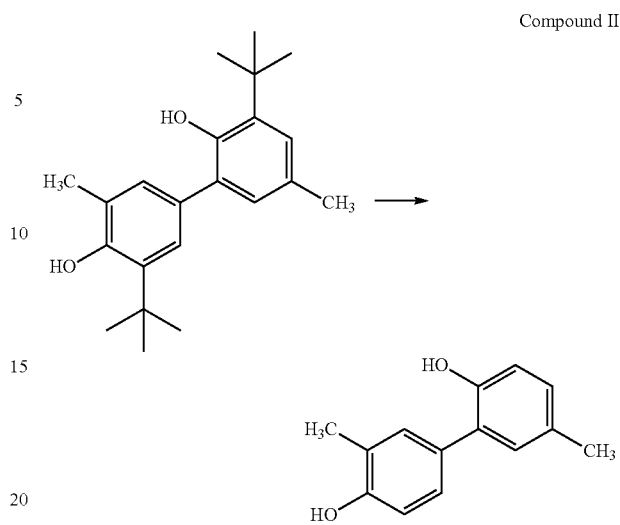

Compound II

The retro-Friedel Crafts alkylation reaction takes place using a Lewis acid catalyst, for example, a metal halide catalyst (e.g., aluminum chloride, ferric chloride) in a suitable solvent. Suitable solvents include anhydrous solvents such as benzene, toluene, DCE, TCE, carbon tetrachloride, and chlorobenzene. In some embodiments, the retro-Friedel crafts alkylation and the phenol cross-coupling occurs in a one-pot reaction, meaning that after the cross-coupling has progressed to a desired extent, the reagent (e.g., aluminum trichloride), is added directly to the existing reaction mixture, and the reaction is continued until the retro-Friedel Crafts has proceeded to a desired extent.

In some embodiments, Method 1 further comprises a "one-pot" combination of the phenolic coupling and dealkylation steps, as described in the preceding paragraphs, wherein the intermediate compound (Compound I) is not isolated.

In some embodiments, Method 1 further comprises the alkylation (e.g., methylation) of the phenolic oxygens of Compound II to yield Compound III:

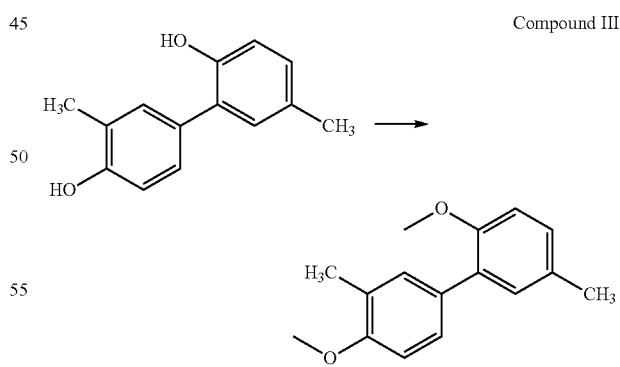

Compound III

The methylation reaction can be performed using conditions known to those skilled in the art, typically comprising a base and a methylating agent in a suitable solvent. Suitable methylating agents include methyl iodide, methyl sulfate (dimethylsulfate), methyl triflate, methyl bromide, and the like. Suitable bases include inorganic bases (such as sodium carbonate, sodium bicarbonate, potassium carbonate, potassium bicarbonate, cesium carbonate, and the like), and organic bases (such as triethylamine, diethylisopropylamine, DBU, DBN, pyridine, methylmorpholine, and the like). Suitable solvents include polar protic and polar aprotic solvents, such as acetonitrile, acetone, tetrahydrofuran, dioxane, dimethoxyethane, and the like.

In some embodiments, Method 1 further comprises a "one-pot" combination of the phenolic coupling, t-butyl dealkylation and the O-alkylation steps, as described in the preceding paragraphs, wherein the intermediate compounds (Compounds I and II) are not isolated. In a particular embodiment, this one-pot combination employs manganese acetylacetonate and oxygen in toluene for the coupling step, aluminum chloride for the dealkylation, and dimethylsulfate with potassium carbonate in acetone for the O-alkylation.

In some embodiments, Method 1 further comprises the benzylic halogenation, e.g., the benzylic bromination, chlorination or iodination, of Compound III to yield Compound IV, wherein X is bromine, chlorine or iodine:

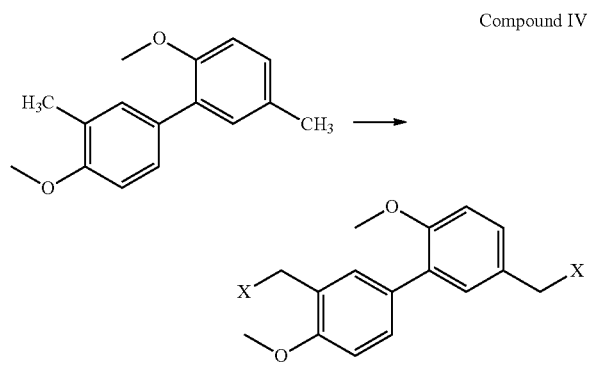

Compound IV

The benzylic halogenation reaction is a free-radical halogenation reaction. The halogenation reaction can be performed using conditions known to those skilled in the art, and typically include a radical initiator and a halogen source, and a suitable solvent. Suitable radical initiators include chemical initiators (e.g., azobisisobutyronitrile or di-tert-butyl peroxide) and physical initiators (e.g., ultraviolet light). Suitable halogen sources include any compounds susceptible to the formation of halogen radicals (e.g., bromine radical, chlorine radical or iodine radical). Such halogen sources include the diatomic halogens (e.g., bromine, chlorine iodine), and compounds that generate the diatomic halogens (e.g., N-bromosuccinimide, N-chlorosuccinimide, N-iodosuccinimide). Suitable solvents include nonpolar solvents and polar aprotic solvents, such as acetonitrile, tetrahydrofuran, dioxane, carbon tetrachloride, TCE, dichloroethane, benzene and chlorobenzene, and the like.

In some embodiments, Method 1 further comprises the coupling of a vinylmetallic agent with Compound IV to yield di-allyl compound V:

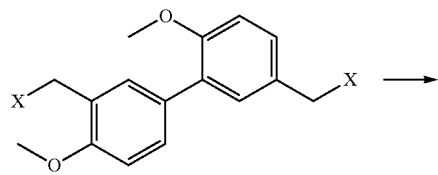

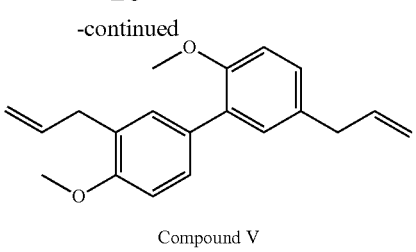

Compound V

The coupling reaction can be performed using conditions known to those skilled in the art, and typically includes a vinyl organometallic agent and optionally a metal catalyst. Typical vinyl reagents include vinyl magnesium bromide, vinyl magnesium chloride, vinyl magnesium iodide, vinyl lithium, and vinyl copper reagents (e.g., divinyl copper lithium). Typical metal catalysts include copper(I) salts such as copper (I) iodide, copper (I) chloride and copper (I) bromide, nickel (II) salts, palladium complexes and iron(III) complexes. Suitable solvents include nonpolar solvents and polar aprotic solvents, such as acetonitrile, tetrahydrofuran, dioxane, dimethoxyethane, diethyl ether, carbon tetrachloride, TCE, dichloroethane, and benzene, and the like.

In some embodiments, Method 1 further comprises the demethylation of Compound V to yield honokiol, and the isolation of the honokiol from the reaction mixture:

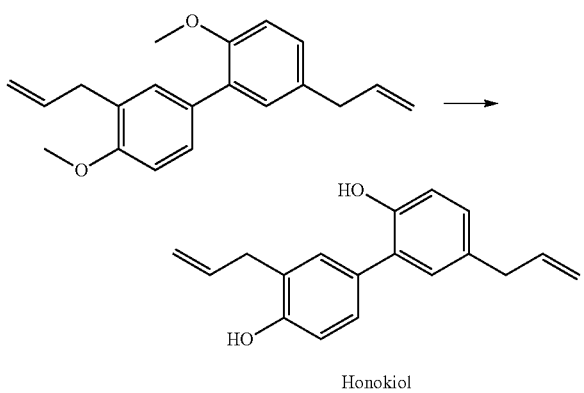

Honokiol

The demethylation reaction can be performed using conditions known to those skilled in the art. Typical reagents include hydrogen iodide, hydrogen bromide, boron tribromide (e.g. boron tribromide-dichloromethane complex, or boron tribromide-dimethyl sulfide complex), boron trichloride, aluminum chloride, aluminum chloride/dimethylsulfide mixture, boron trifluoride, and iodotrimethylsilane, as well as combinations and mixtures with halide sources such as sodium iodide. Suitable solvents for the reaction vary and depend on the reagent chosen, but can include, for example, dichloromethane, acetonitrile, dichloroethane, toluene and carbon tetrachloride.

In some embodiments, Method 1 comprises each of the above steps according to the details described above.

In some embodiments, honokiol produced according to Method 1 as described above (or Method 3, as described below) is used as chemical intermediate in the synthesis of useful derivatives of honokiol, such as dihydrohonokiols, tetrahydrohonokiol, mono- and di-epoxides of honokiol, and other derivatives as well as derivatives thereof.

In another embodiment, the present disclosure provides a method of making honokiol comprising the use of 3,3'-di-tert-butyl-5,5'-dimethyl-[1,1'-biphenyl]-2,4'-diol (Compound I):

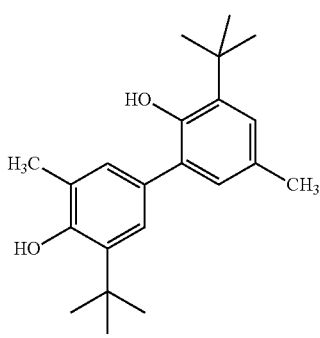 [SMILES: Cc1cc(-c2cc(C)c(O)c(C(C)(C)C)c2)c(O)c(C(C)(C)C)c1]

In another embodiment, the present disclosure provides for the use of Compound I in making honokiol.

In another embodiment, the present disclosure provides a method of making honokiol comprising the use of 3',5-dimethyl-[1,1'-biphenyl]-2,4'-diol (Compound II):

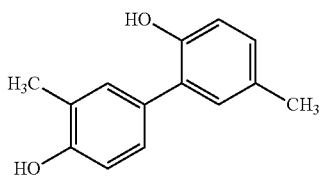

In another embodiment, the present disclosure provides for the use of Compound II in making honokiol.

In another embodiment, the present disclosure provides a method of making honokiol comprising the use of 2,4'-dimethoxy-3',5-dimethyl-1,1'-biphenyl (Compound III):

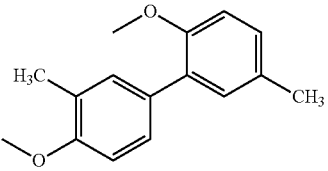

In another embodiment, the present disclosure provides for the use of Compound III in making honokiol.

In another embodiment, the present disclosure provides a method of making honokiol comprising the use of a 3',5-bis(halomethyl)-2,4'-dimethoxy-1,1'-biphenyl (Compound IV), wherein X is bromo, chloro or iodo:

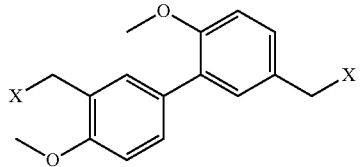

For example, a method of making honokiol comprising the use of a 3',5-bis(bromomethyl)-2,4'-dimethoxy-1,1'-biphenyl (Compound IVa):

In another embodiment, the present disclosure provides for the use of Compound IV, wherein X is bromo, chloro or iodo, e.g., Compound IVa, in making honokiol.

In another aspect, the present disclosure provides a method (Method 2) of making 3,3'-di-tert-butyl-5,5'-dimethyl-[1,1'-biphenyl]-2,4'-diol (Compound I) comprising the reaction of 2-tert-butyl-6-methylphenol with 2-tert-butyl-4-methylphenol, as shown below:

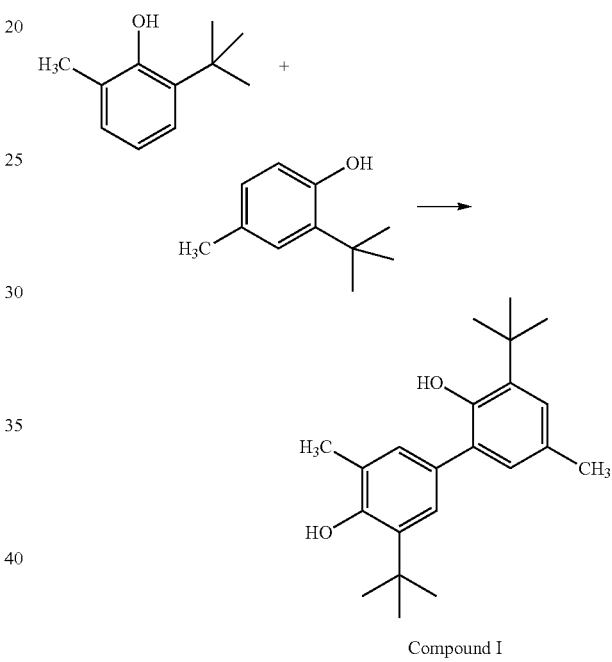

Compound I

This reaction is an example of a catalytic oxidative phenol cross-coupling between a 2,6-disubstituted phenol and a 2,4-disubstituted phenol. The reaction is difficult because the catalyst must promote the cross-coupling reaction at a significantly faster rate than the two competing homo-coupling reactions.

Suitable catalysts for this oxidative phenol cross-coupling reaction include metal catalyst systems in which the metal is readily reoxidized by diatomic oxygen. Such metals include chromium (Cr), copper (Cu), iron (Fe), manganese (Mn), ruthenium (Ru) and vanadium (V). In selected embodiments, the metal is chromium or manganese. The metal is employed as part of a complex in which the metal is coordinated to an amine or imine scaffold, for example, a salan (N,N'-ethylenebis(salicylamine)) or salen (N,N'-ethylenebis(salicylimine) scaffold. In some embodiments, the phenyl rings of the salan or salen ligand are substituted with an ortho-alkyl group, e.g., an ortho t-butyl group. In some embodiments, the ethylene bridge of the scaffold is substituted, e.g., 1,2-trans-dialkyl, 1,2-trans-diaryl, or 1,2-trans-fused cycloalkane. In selected embodiments, the scaffold is a Salan-Ph or Salen-Ph (1,2-trans-diphenyl bridge), or Salan-Cy or Salen-Cy (1,2-trans fused cyclohexane bridge). In one embodiment the catalyst complex is selected from Cr-Salen-Cy, Mn-Salen-Ph, or Cu-Salen-Cy. These are relatively inexpensive metal catalysts. In selected embodiments, the catalyst is Cr-Salen-Cy.

The oxidative phenol cross-coupling reaction is carried out in a suitable solvent or mixture of solvents and in the presence of an oxidant. Suitable solvents include dichloroethane (DCE), tetrachloroethane (TCE), carbon tetrachloride, benzene, toluene, trifluoromethylbenzene, chlorobenzene, dichlorobenzene, and other highly nonpolar aliphatic and aromatic solvents, or mixtures thereof. In some embodiments, the solvent is dichloroethane. The reaction mixture must comprise an oxidant which is capable of reoxidizing the consumed metal center (e.g., Cr(III)) back to its higher oxidation state (e.g., Cr(IV)). The oxidant can be any species capable of performing this oxidation, for example, air, diatomic oxygen ($O_2$), ozone, peroxides (e.g., hydrogen peroxide, di-tert-butyl peroxide), hydroperoxides (e.g., tert-butylhydroperoxide), peroxy acids (e.g., peracetic acid, peroxymonosulfuric acid, meta-chloroperoxybenzoic acid, trifluoroperacetic acid, performic acid), inorganic oxidizing agents (e.g., sodium hypochlorite, sodium chlorite, sodium chlorate, sodium perchlorate, potassium permanganate, manganese dioxide, selenium dioxide, chromate salts, dichromate salts, silver (I) acetate, sodium periodate, sodium bromate, etc.) and other organic oxidizing agents (e.g., iodosobenzene, iodoxybenzoic acid and other hypervalent iodine reagents). In selected embodiments, the oxidant is oxygen.

In some embodiments, Method 2 further comprises the retro-Friedel Crafts alkylation of Compound I to yield Compound II:

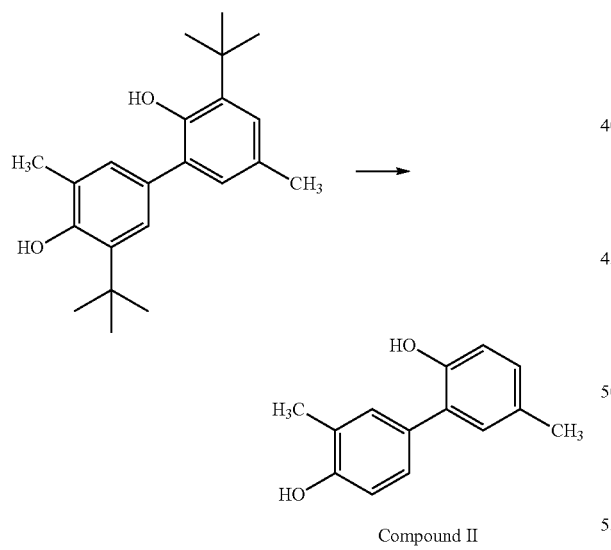

Compound II

The retro-Friedel Crafts alkylation reaction takes place using a Lewis acid catalyst, for example, a metal halide catalyst (e.g., aluminum chloride, ferric chloride) in a suitable solvent. Suitable solvents include anhydrous solvents such as benzene, toluene, DCE, TCE, carbon tetrachloride, and chlorobenzene. In some embodiments, the retro-Friedel crafts alkylation and the phenol cross-coupling occurs in a one-pot reaction, meaning that after the cross-coupling has progressed to a desired extent, the reagent (e.g., aluminum trichloride), is added directly to the existing reaction mixture, and the reaction is continued until the retro-Friedel Crafts has proceeded to a desired extent.

In another aspect, the present disclosure provides a novel compound selected from Compound I, Compound II, and/or Compound III. In another aspect, the present disclosure provides a novel compound of the structure of Compound IV wherein X is bromo, chloro or iodo.

In another aspect, the present disclosure provides any one or more of Compound I, Compound II, Compound III or Compound IV (e.g., wherein X is bromo, chloro or iodo) for use in the manufacture of Honokiol.

In another aspect, the present disclosure provides any one or more of Compound I, Compound II, Compound III or Compound IV (e.g., wherein X is bromo, chloro or iodo) for use in the manufacture of a medicament comprising Honokiol. In some embodiments that medicament is a consumer product, e.g., an oral care product, a personal care product, or a home care product, for example, a dentifrice, toothpaste, oral gel, mouthwash, mouthrinse, tooth powder, sunscreen, antiperspirant, deodorant, shampoo, bar soap, body soap, body wash, skin cream, skin lotion, moisturizing lotion, liquid soap, dishwashing liquid, laundry detergent, or home cleaning liquid.

In another embodiment, the present disclosure provides a method (Method 3) of making honokiol comprising the reaction of 2,6-di-tert-butylphenol with 2,4-di-tert-butylphenol to yield 3,3',5,5'-tetra-tert-butyl-[1,1'-biphenyl]-2,4'-diol (Compound VI), as shown below:

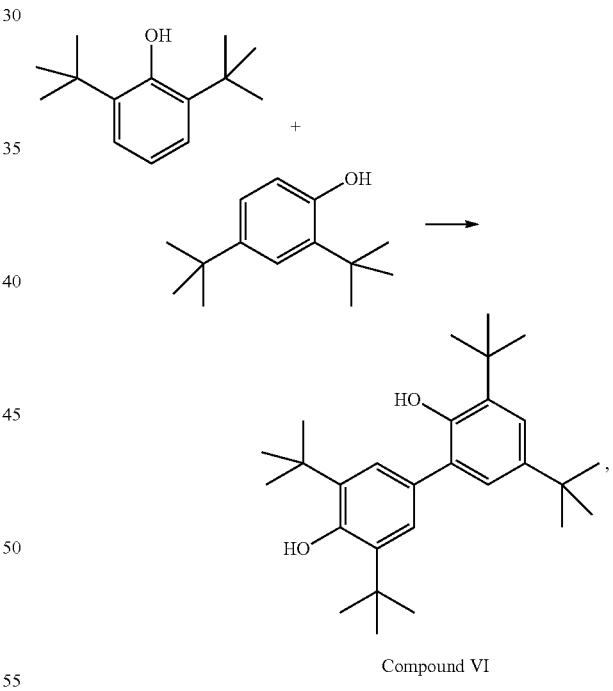

Compound VI followed by the isolation of Honokiol.

This reaction is also an example of a catalytic oxidative phenol cross-coupling between a 2,6-disubstituted phenol and a 2,4-disubstituted phenol. As with the reaction to make Compound I, the reaction to make Compound VI is difficult because the catalyst must promote the cross-coupling reaction at a significantly faster rate than the two competing homo-coupling reactions. Conditions for this reaction are described supra.

In some embodiments, Method 3 further comprises, in any order, one or more of the following steps: dealkylation of the four t-butyl groups of Compound VI, alkylation of the two phenolic oxygens of Compound VI or VII, electrophilic aromatic halogenation of the Compound VI, VII or VIII, substitution of the halogens of Compound IX or the halo derivative of Compound VI, VII or VIII with an allyl reagent (e.g., an allyl organometallic reagent or allyl halide), and dealkylation of the alkyl ether groups of Compound V or the allyl derivatives of Compound VI, VII, VIII.

In a particular embodiment, Method 3 further comprises the following steps in order as shown in the scheme below: the dealkylation of the t-butyl groups of Compound VI to yield Compound VII, the alkylation of the phenolic oxygens of Compound VII to yield Compound VIII-A, the electrophilic aromatic halogenation of Compound VIII-A to yield Compound IX-A, the allyl substitution of Compound IX-A to yield Compound V-A, and the dealkylation of Compound V-A to yield Honokiol, and isolation thereof. In Compounds VIII-A, IX-A and V-A, R may be any $C_{1-6}$ alkyl group, including straight-chain, branched and/or substituted, e.g., substituted with one or more $C_{1-6}$ alkyl ethers or substituted with one or more $C_{1-6}$ alkyl or aryl ether or mixed silyl ethers. Examples of such R groups include, but are not limited to, methyl, ethyl, propyl, isopropyl, t-butyl, benzyl, methoxymethyl, benzyloxymethyl, 2-methoxyethoxymethyl, 1-ethoxyethyl, 2-trimethylsilylethyl, trimethylsilyl, triethylsilyl, triisopropylsilyl, t-butyldimethylsilyl, t-butyldiphenylsilyl, diphenylmethylsilyl, di-t-butylmethylsilyl, and the like.

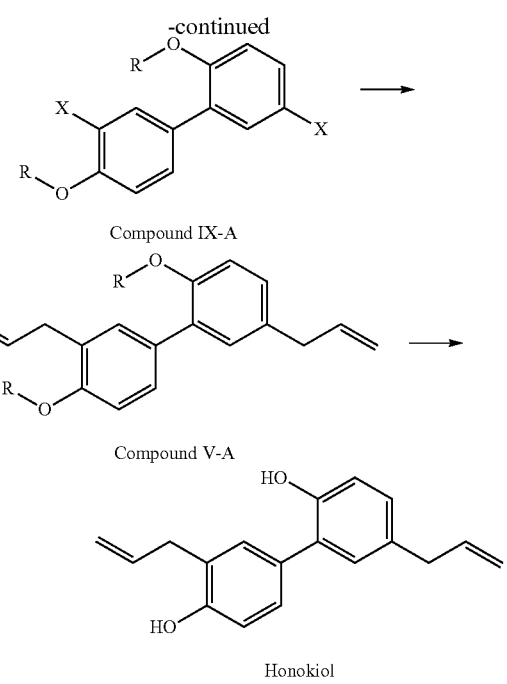

Compound IX-A

Compound V-A

Honokiol

In some embodiments, Method 3 further comprises the dealkylation of Compound VI to yield Compound VII (e.g., a retro Friedel Crafts alkylation):

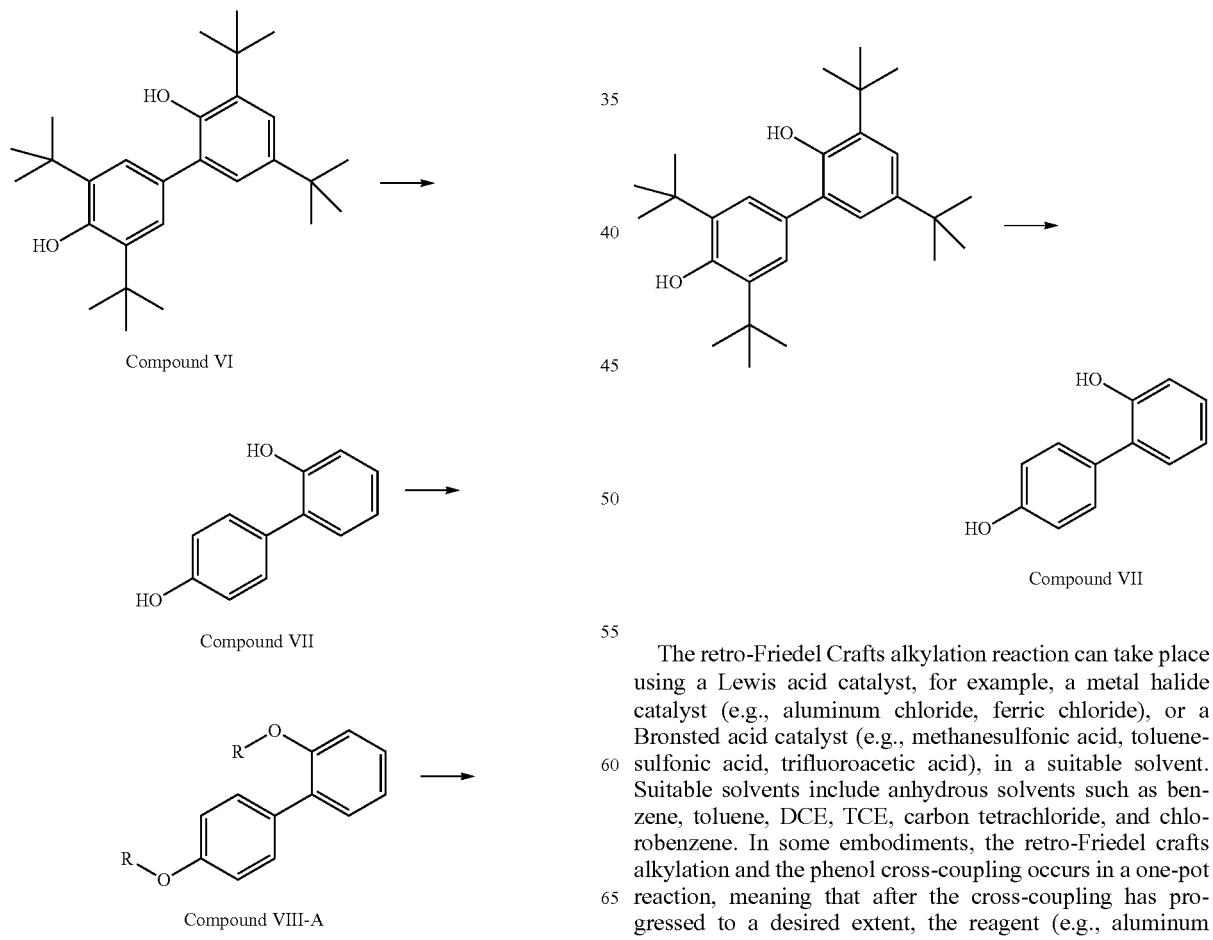

Compound VI

Compound VII

Compound VIII-A

Compound VII

The retro-Friedel Crafts alkylation reaction can take place using a Lewis acid catalyst, for example, a metal halide catalyst (e.g., aluminum chloride, ferric chloride), or a Bronsted acid catalyst (e.g., methanesulfonic acid, toluenesulfonic acid, trifluoroacetic acid), in a suitable solvent. Suitable solvents include anhydrous solvents such as benzene, toluene, DCE, TCE, carbon tetrachloride, and chlorobenzene. In some embodiments, the retro-Friedel crafts alkylation and the phenol cross-coupling occurs in a one-pot reaction, meaning that after the cross-coupling has progressed to a desired extent, the reagent (e.g., aluminum trichloride), is added directly to the existing reaction mixture, and the reaction is continued until the retro-Friedel Crafts has proceeded to a desired extent.

In some embodiments, Method 3 further comprises a "one-pot" combination of the phenolic coupling and dealkylation steps, as described in the preceding paragraphs, wherein the intermediate compound (Compound VI) is not isolated.

In some embodiments, Method 3 further comprises the alkylation (e.g., methylation) of the phenolic oxygens of Compound VII to yield Compound VIII:

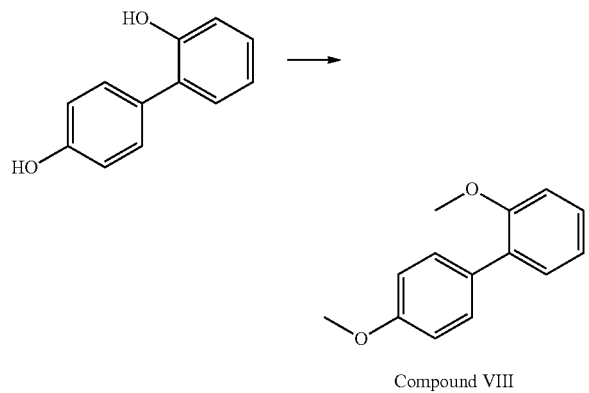

Compound VIII

The methylation reaction can be performed using conditions known to those skilled in the art, typically comprising a base and a methylating agent in a suitable solvent. Suitable methylating agents include methyl iodide, methyl sulfate (dimethylsulfate), methyl triflate, methyl bromide, and the like. Suitable bases include inorganic bases (such as sodium carbonate, sodium bicarbonate, potassium carbonate, potassium bicarbonate, cesium carbonate, and the like), and organic bases (such as triethylamine, diethylisopropylamine, DBU, DBN, pyridine, methylmorpholine, and the like). Suitable solvents include polar protic and polar aprotic solvents, such as acetonitrile, acetone, tetrahydrofuran, dioxane, dimethoxyethane, and the like.

In some embodiments, Method 3 further comprises a "one-pot" combination of the phenolic coupling, t-butyl dealkylation and the O-alkylation steps, as described in the preceding paragraphs, wherein the intermediate compounds (Compounds VI and VII) are not isolated.

In some embodiments, Method 3 further comprises the electrophilic aromatic halogenation, e.g., bromination, chlorination or iodination, of Compound VIII to yield Compound IX, wherein X is bromine, chlorine or iodine:

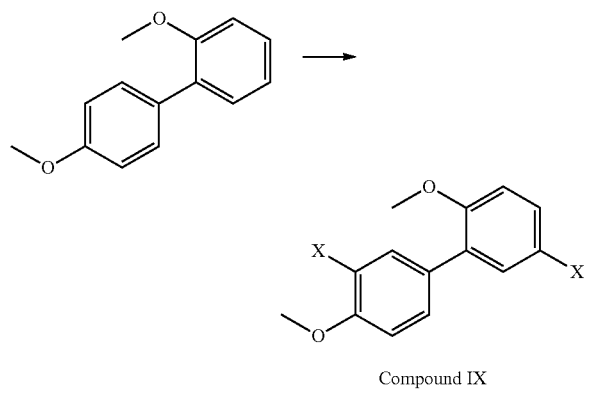

Compound IX

The aromatic halogenation reaction can be performed using conditions known to those skilled in the art, and often includes a radical initiator and a halogen source, and a suitable solvent. Suitable radical initiators include chemical initiators (e.g., azobisisobutyronitrile, hydrogen peroxide, or di-tert-butyl peroxide). Suitable halogen sources include the diatomic halogens (e.g., bromine, chlorine, iodine), as well as halide salts (e.g., Iron (III) halides) and compounds that generate the diatomic halogens (e.g., N-bromosuccinimide, N-chlorosuccinimide, N-iodosuccinimide). Suitable solvents include acidic solvents such as acetic acid.

In some embodiments, Method 3 further comprises the coupling of an allyl reagent with Compound IX to yield di-allyl compound V:

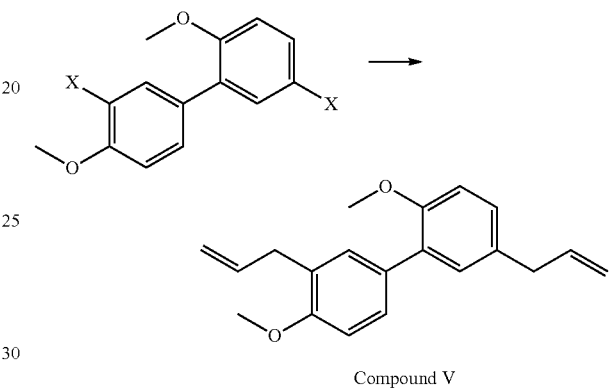

Compound V

The coupling reaction can be performed using conditions known to those skilled in the art. In one embodiment, the reaction is a Kumar Grignard/allyl Kumada-type coupling. In this reaction, the aromatic halide (e.g. bromide) is converted into an organometallic reagent (e.g., a lithium or magnesium halide, e.g., magnesium bromide) by reaction with a suitable reagent (e.g., magnesium with catalytic iodine). The reactive organometallic reagent can then be coupled to an allyl halide, such as allyl bromide, using a palladium (0) catalyst, such as tetrakis(triphenylphosphine) palladium, in a suitable solvent, such as THF.

In another embodiment, the allyl coupling is carried out by reacting the aromatic bromide with an allyl organometallic agent (e.g., allyl lithium, allyl magnesium bromide, allyl magnesium chloride, or allyl magnesium iodide) in the presence of a palladium catalyst and optionally a ligand. In a single reaction step, the palladium reagent catalyses substitution of the aromatic halide by the allyl group. Suitable palladium reagents include palladium acetate, optionally with a suitable ligand, such as a phosphine ligand (e.g., X-Phos or BrettPhos). In another embodiment, this reaction is followed by further treatment with an allyl halide, e.g., allyl bromide. In some embodiments, treatment with the allyl organometallic agent (e.g., allyl magnesium bromide or chloride) converts some portion of the para-positioned bromo group of Compound IX into an organometallic group. For example, treatment with allyl magnesium bromide results in formation of some of bromomagnesium compound, i.e., a metallic insertion occurs rather than a direct coupling. When this occurs, however, treatment of the reaction mixture with additional allyl halide (e.g., allyl bromide or allyl chloride) will result in conversion of this organometallic intermediate to the desired direct coupling product, as shown below.

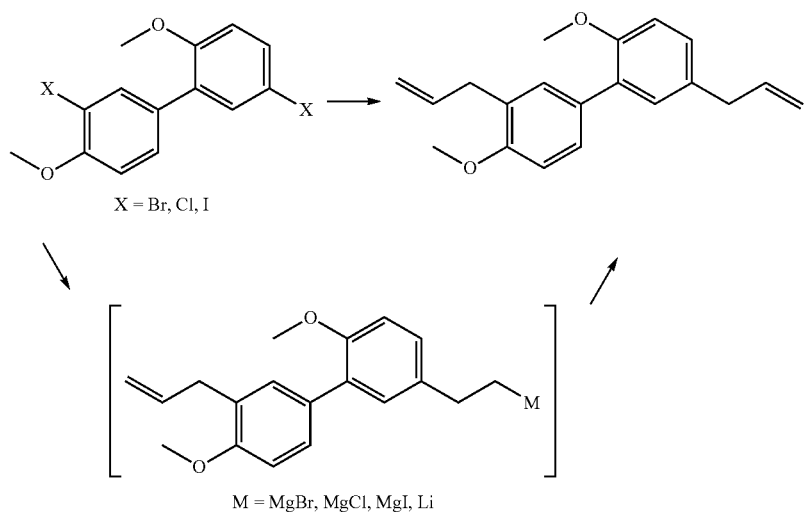

In some embodiments, Method 3 further comprises the demethylation of Compound V to yield honokiol, as described supra.

In another embodiment, the present disclosure provides a method of making honokiol comprising the use of 3,3',5,5'-di-tert-butyl-5,5'-[1,1'-biphenyl]-2,4'-diol (Compound VI):

In another embodiment, the present disclosure provides for the use of Compound VI in making honokiol.

In another embodiment, the present disclosure provides a method of making honokiol comprising the use of 1,1'-biphenyl-2,4'-diol (Compound VII):

In another embodiment, the present disclosure provides for the use of Compound VII in making honokiol.

In another aspect, the present disclosure provides a method (Method 4) of making 3,3',5,5'-di-tert-butyl-[1,1'-biphenyl]-2,4'-diol (Compound VI) comprising the reaction of 2,6-di-tert-butylphenol with 2,4-di-tert-butylphenol, as shown below:

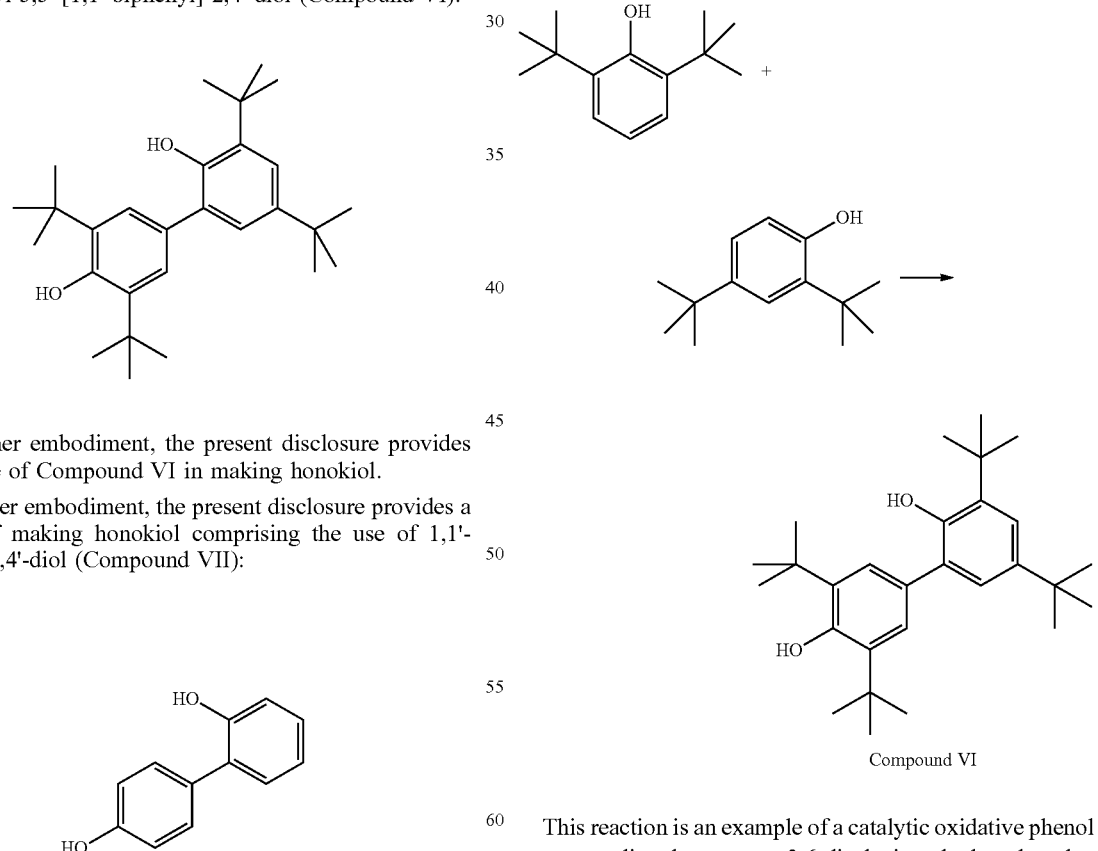

This reaction is an example of a catalytic oxidative phenol cross-coupling between a 2,6-disubstituted phenol and a 2,4-disubstituted phenol. The conditions for this reaction are as described supra.

In some embodiments, Method 4 further comprises the retro-Friedel Crafts alkylation of Compound VI to yield Compound VII:

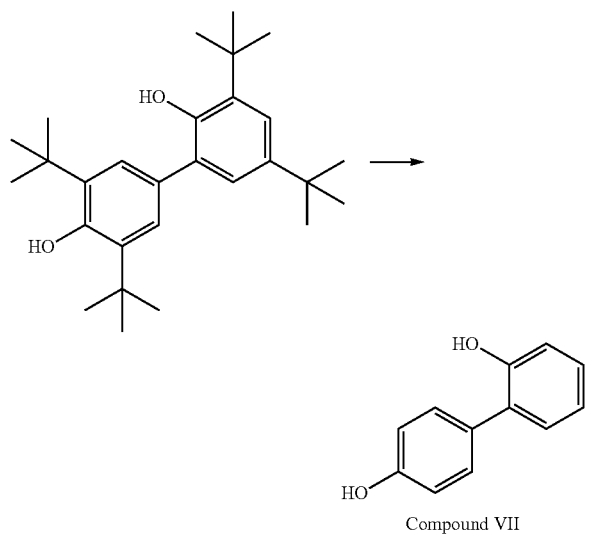

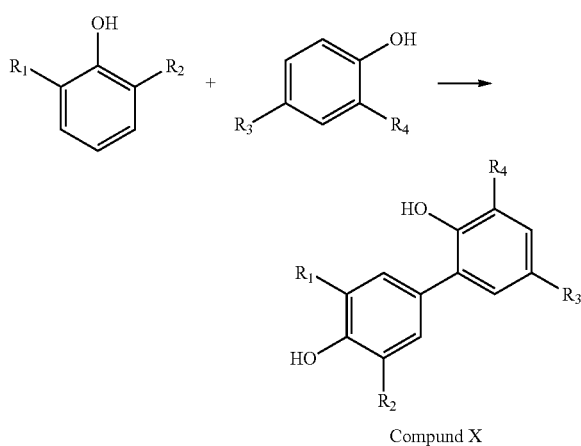

Compound VII

Conditions for the retro-Friedel Crafts alkylation to form Compound VII are described supra.

In another aspect, the present disclosure provides Compound VI, for use in the manufacture of Honokiol. In another aspect, the present disclosure provides Compound VI for use in the manufacture of a medicament comprising Honokiol. In some embodiments that medicament is a consumer product, e.g., an oral care product, a personal care product, or a home care product, for example, a dentifrice, toothpaste, oral gel, mouthwash, mouthrinse, tooth powder, sunscreen, antiperspirant, deodorant, shampoo, bar soap, body soap, body wash, skin cream, skin lotion, moisturizing lotion, liquid soap, dishwashing liquid, laundry detergent, or home cleaning liquid.

In another aspect, the present disclosure provides a method (Method 5) of making a tetrasubstituted bisphenol (Compound X) comprising the reaction of a disubstituted phenol with a second disubstituted phenol, as shown below:

Compund X wherein the reaction comprises the use of a metal catalyst, and wherein $R_1$, $R_2$, $R_3$ and $R_4$ are each independently a $C_{1-10}$ alkyl, $C_{1-10}$ alkylene, or $C_{1-10}$ alkynylene, optionally substituted with ether, sulfide, ester, amide, halide, nitrile or amino groups, and wherein the $C_{1-10}$ backbone is optionally straight or branched. In some embodiments, $R_1$, $R_2$, $R_3$ and $R_4$ are each independently a $C_{1-10}$ alkyl. In some embodiments, $R_1$, $R_2$, $R_3$ and $R_4$ are each independently a $C_{1-4}$ alkyl group, optionally straight or branched (e.g., methyl, ethyl, propyl, isopropyl, butyl, isobutyl, sec-butyl, or t-butyl).

This reaction is an example of a catalytic oxidative phenol cross-coupling between a 2,6-disubstituted phenol and a 2,4-disubstituted phenol. The conditions for this reaction are as described supra.

The invention will be described in greater detail by way of specific examples. The following examples are offered for illustrative purposes and are not intended to limit the scope of the invention in any manner Those of skill in the art will readily recognize a variety of non-critical parameters which can be changed or modified to yield essentially the same results.

EXAMPLES

The reaction described herein can be carried out as described in the following paragraphs. The compounds described herein can be prepared according to the procedures described in the following paragraphs.

Example 1

Compound II (3',5-dimethyl-[1,1'-biphenyl]-2,4'-diol)

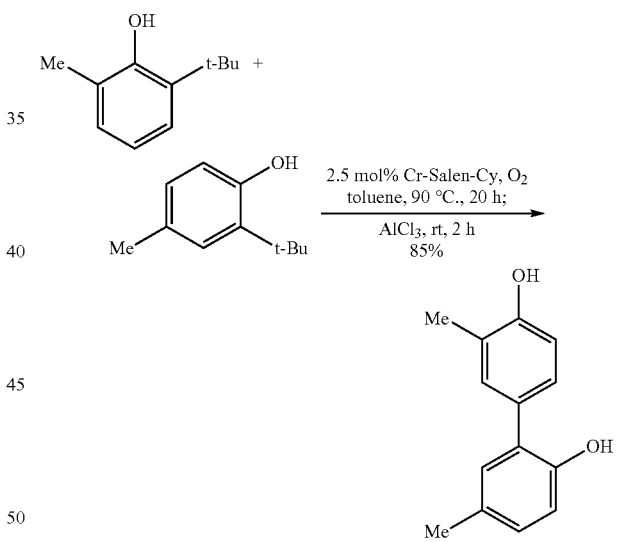

To a 100 mL flask equipped with a reflux condenser is added 2-tert-butyl-6-methylphenol (657 mg, 4.0 mmol), 2-tert-butyl-4-methylphenol (788 mg, 4.8 mmol), Cr-Salen-Cy catalyst (63 mg, 0.1 mmol) and distilled toluene (20 mL, 0.2 M). The reaction mixture is purged with oxygen and heated to 90° C. under an oxygen atmosphere for 20 h. The mixture is cooled to ambient temperature. To the resultant solution of Compound I (3, 3'-di-tert-butyl-5,5'-dimethyl-[1,1'-biphenyl]-2,4'-diol) is added aluminum chloride (1.1 g, 8.8 mmol) slowly over 5 minutes at 0° C., and the mixture is allowed to warm over 30 minutes to ambient temperature. After being stirred at ambient temperature for a further 2 h, the reaction mixture is quenched by addition of 30 mL of 1 N HCl solution at 0° C. The mixture is then thoroughly extracted with dichloromethane (2×20 mL). The combined organic layers are concentrated by rotary evaporation. The resultant residue is purified by chromatography (silica) using 5% ethyl acetate/hexane as the eluent to afford Compound II (728 mg, 3.4 mmol, 85% yield) as a brown crystalline solid: $^1$H NMR (500 MHz, CDCl$_3$) δ 7.21 (d, J=2.0 Hz, 1H), 7.16 (dd, J=8.5, 2.0 Hz, 1H), 7.03 (dd, J=8.5 Hz, 2.0 Hz, 1H), 7.01 (d, J=2.0 Hz, 1H), 6.87 (d, J=8.0 Hz, 2H), 5.07 (s, 1H), 4.91 (s, 1H), 2.30 (s, 6H); $^{13}$C NMR (125 MHz, CDCl$_3$) δ 153.6, 150.2, 131.7, 130.6, 129.8, 129.5, 129.2, 127.8, 127.6, 124.8, 115.6, 115.4, 20.5, 15.8; IR (film) 3402, 3026, 2922, 1611, 1496, 1456, 1384, 1118, 818 cm$^{-1}$; HRMS (ESI) m/z=213.0916 calcd for C$_{14}$H$_{13}$O$_2$ [M−H]$^−$, found 213.0924.

Example 2-1

Compound III (2,4'-dimethoxy-3',5-dimethyl-1,1'-biphenyl)

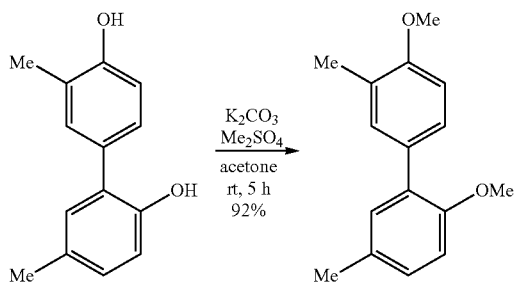 [SMILES: Cc1ccc(O)c(-c2ccc(O)c(C)c2)c1 ; COc1ccc(-c2cc(C)ccc2OC)cc1C]

To a stirred solution of Compound II (728 mg, 3.4 mmol) in acetone (17 mL, 0.2 M) is added anhydrous potassium carbonate (1.4 g, 10.2 mmol, 3.0 equiv). After stirring at ambient temperature for 10 min, dimethylsulfate (0.81 mL, 8.5 mmol, 2.5 equiv) is added and the reaction mixture is stirred for 5 hours at ambient temperature. The reaction is quenched with deionized water (50 mL) and the acetone is removed by rotary evaporation. Ethyl acetate (20 mL) is added and the organic layer separated. The aqueous layer is extracted with additional ethyl acetate (2×20 mL). The combined organic layers are washed with water and brine, dried (sodium sulfate), and concentrated by rotary evaporation. The residue is purified by column chromatography (silica) using hexane/ethyl acetate (9:1) as the eluent to afford Compound III (758 mg, 3.13 mmol, 92%) as white solid: $^1$H NMR (500 MHz, CDCl$_3$) δ 7.37 (dd, J=8.0 Hz, 2.0 Hz, 1H), 7.29 (d, J=2.0 Hz, 1H), 7.10 (d, J=2.0 Hz, 1H), 7.07 (dd, J=8.0 Hz, 2.0 Hz, 1H), 6.87 (d, J=1.5 Hz, 1H), 6.86 (d, J=1.5 Hz, 1H), 3.89 (s, 3H), 3.81 (s, 3H), 2.36 (s, 3H), 2.30 (s, 3H); $^{13}$C NMR (125 MHz, CDCl$_3$) δ 157.0, 154.6, 132.0, 131.6, 130.8, 130.5, 130.1, 128.4, 128.0, 126.2, 111.4, 109.7, 55.9, 55.5, 20.7, 16.5; IR (film) 3437, 2949, 2834, 1609, 1495, 1463, 1242, 1135, 1033, 810, 741 cm$^{-1}$; HRMS (ESI) m/z=243.1385 calcd for C$_{16}$H$_{19}$O$_2$ [M+H]$^+$, found 243.1384.

Example 2-2

Compound III (2,4'-dimethoxy-3',5-dimethyl-1,1'-biphenyl)

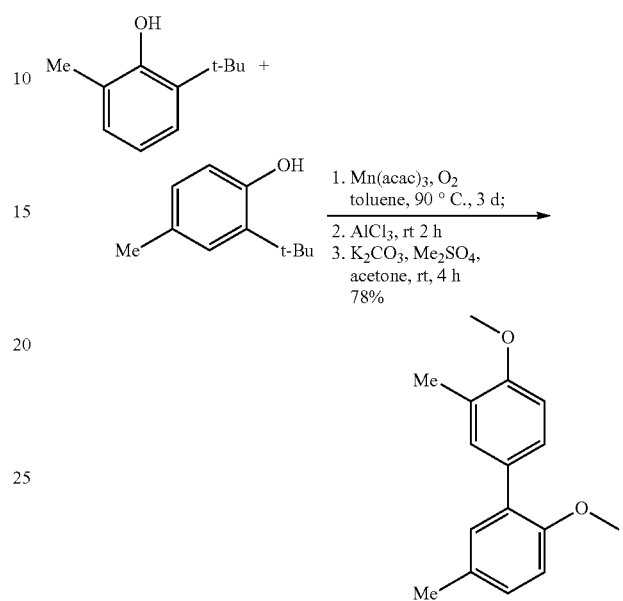

To a 500 mL flask equipped with a reflux condenser is added 2-tert-butyl-6-methylphenol (4.9 g, 30 mmol), 2-tert-butyl-4-methylphenol (5.9 g, 36 mmol), Mn(acac)$_3$ (1.0 g, 3.0 mmol) and distilled toluene (150 mL, 0.2 M). The reaction mixture is purged with oxygen and heated to 90° C. under an oxygen atmosphere for 3 days. The mixture is then cooled to ambient temperature to yield a solution of Compound I.

To the resultant solution of Compound I is added aluminum chloride (8.8 g, 66 mmol) slowly over 5 minutes at 0° C., and the mixture is allowed to warm over 30 minutes to ambient temperature. After being stirred at room temperature for 2 hours, the reaction mixture is quenched by addition of 30 mL of 1 N HCl solution at 0° C. The mixture is extracted with CH$_2$Cl$_2$ (2×50 mL) and the combined organic layers are concentrated by rotary evaporation to yield crude Compound II.

To a stirred solution of crude Compound II in acetone (150 mL, 0.2 M) is added anhydrous potassium carbonate (11.6 g, 84 mmol). After stirring at ambient temperature for 10 min, dimethylsulfate (7.1 mL, 75 mmol) is added and the reaction mixture is stirred for 4 hours at ambient temperature. The reaction is quenched with deionized water (50 mL) and the acetone is removed by rotary evaporation. Ethyl acetate (50 mL) is added and the organic layer separated. The aqueous layer is extracted with ethyl acetate (2×50 mL). The combined organic layers are washed with brine (100 mL), dried with sodium sulfate, and concentrated by rotary evaporation. The residue is purified by column chromatography using hexane/ethyl acetate (9:1) as the eluent to afford Compound III (5.7 g, 23.5 mmol, 78% overall) as a pale yellow liquid: $^1$H NMR (500 MHz, CDCl$_3$) δ 7.37 (dd, J=8.0 Hz, 2.0 Hz, 1H), 7.29 (d, J=2.0 Hz, 1H), 7.10 (d, J=2.0 Hz, 1H), 7.07 (dd, J=8.0 Hz, 2.0 Hz, 1H), 6.87 (d, J=1.5 Hz, 1H), 6.86 (d, J=1.5 Hz, 1H), 3.89 (s, 3H), 3.81 (s, 3H), 2.36 (s, 3H), 2.30 (s, 3H); $^{13}$C NMR (125 MHz, CDCl$_3$) δ 157.0, 154.6, 132.0, 131.6, 130.8, 130.5, 130.1, 128.4, 128.0, 126.2, 111.4, 109.7, 55.9, 55.5, 20.7, 16.5; IR (film) 3437, 2949, 2834, 1609, 1495, 1463, 1242, 1135, 1033, 810, 741 cm$^{-1}$; HRMS (ESI) m/z=243.1385 calcd for $C_{16}H_{19}O_2$ [M+H]$^+$, found 243.1384.

Example 3

Compound IVa (3',5-bis(Bromomethyl)-2,4'-dimethoxy-1,1'-biphenyl)

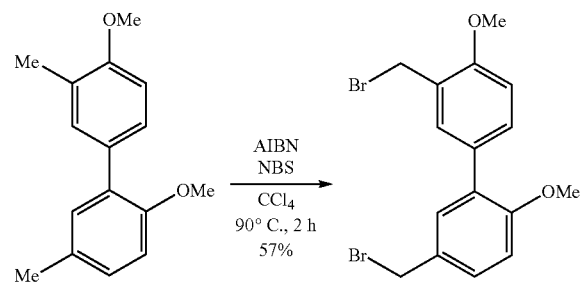 [SMILES: COc1ccc(-c2cc(C)ccc2OC)cc1C ; COc1ccc(-c2cc(CBr)ccc2OC)cc1CBr]

Compound III (758 mg, 3.13 mmol), azobisisobutyronitrile (26 mg, 0.16 mmol) and N-bromosuccinimide (1.11 g, 6.26 mmol, crystallized from water) are dissolved in carbon tetrachloride (15 mL). The reaction mixture is heated to 85° C. and stirred for 2 h under an argon atmosphere. The solution is filtered and the solvent is removed by rotary evaporation. The residue is purified by column chromatography (silica) using 5% ethyl acetate/hexane as the eluent to afford Compound IVa (720 mg, 1.8 mmol, 57% yield) as a yellow solid: $^1$H NMR (500 MHz, CDCl$_3$) δ 7.50 (d, J=2.3 Hz, 1H), 7.47 (dd, J=8.5 Hz, 2.3 Hz, 1H), 7.34-7.32 (m, 2H), 6.94 (d, J=8.5 Hz, 1H), 6.92 (d, J=8.5 Hz, 1H), 4.62 (s, 2H), 4.54 (s, 2H), 3.94 (s, 3H), 3.82 (s, 3H); $^{13}$C NMR (125 MHz, CDCl$_3$) δ 156.7, 156.5, 132.0, 131.5, 131.2, 130.2, 130.1, 130.0, 129.2, 125.6, 111.3, 110.6, 55.7, 33.9, 29.1; IR (film) 3437, 2959, 1608, 1495, 1462, 1251, 1216, 1147, 1027, 818, 738 cm$^{-1}$.

Example 4-1 (Small Scale)

Compound V (3',5-diallyl-2,4'-dimethoxy-1,1'-biphenyl)

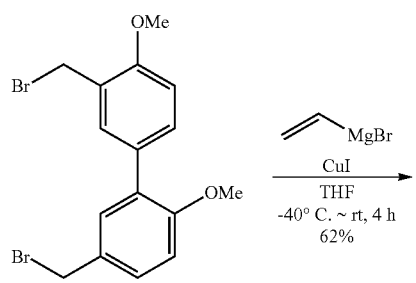

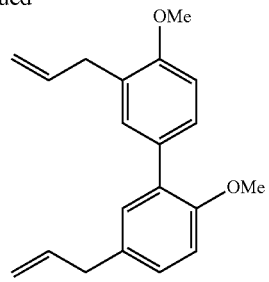

To a solution of copper (I) iodide (26 mg, 0.14 mmol) and Compound IVa (110 mg, 0.28 mmol) in distilled tetrahydrofuran (10 mL) at −10° C., a solution of vinylmagnesium bromide, 1.0 M in tetrahydrofuran (1.1 mL) is slowly added under an argon atmosphere. The mixture is stirred at ambient temperature for 4 hours. The reaction is then quenched by the addition of 15 mL of deionized water. The mixture is extracted with diethyl ether (2×15 mL). The combined organic layers are dried with anhydrous sodium sulfate and filtered. After removal of the solvent by rotary evaporation, the residue is purified by column chromatography (silica) using 5% ethyl acetate/hexane as the eluent to give Compound V (50 mg, 0.17 mmol, 62% yield) as a clear oil: $^1$H NMR (500 MHz, CDCl$_3$) δ 7.37 (dd, 1H, J=8.5, 2.0 Hz), 7.31 (d, 1H, J=2.0 Hz), 7.11 (d, 1H, J=2.0 Hz), 7.09 (dd, 1H, J=8.5, 2.0 Hz), 6.91 (s, 1H), 6.89 (s, 1H), 5.96-6.01 (m, 2H), 5.03-5.11 (m, 4H), 3.86 (s, 3H), 3.78 (s, 3H), 3.43 (d, 2H, J=6.5 Hz), 3.37 (d, 2H, J=6.5 Hz).

Example 4-2 (Large Scale)

Compound V (3',5-diallyl-2,4'-dimethoxy-1,1'-biphenyl)

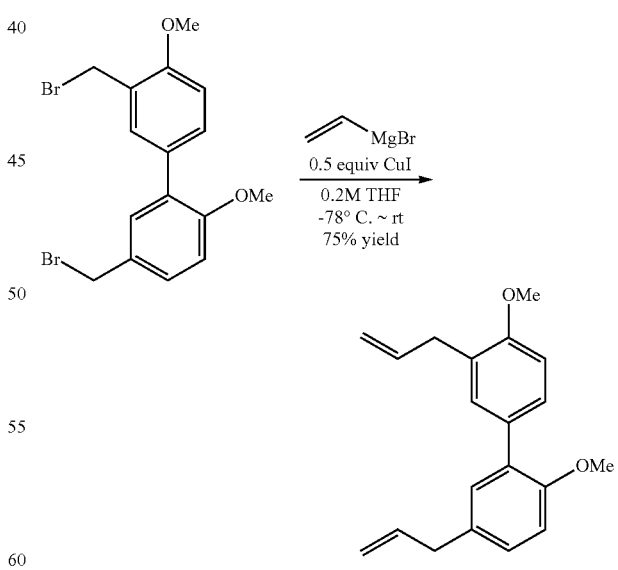

To a solution of CuI (286 mg, 1.5 mmol) and Compound IV (1.2 g, 3.0 mmol) in dry THF (15 mL) at −78° C., a solution of vinylmagnesium bromide (12 mL, 1.0 M in THF) was slowly added at a rate of 3 mL/min using syringe pump under an argon atmosphere. The resulting mixture was allowed to warm to ambient and was stirred for 8 h. The reaction was then quenched by addition of 15 mL of saturated NH₄Cl solution. The mixture was extracted with diethyl ether (15 mL×2). The combined organic layers were dried with anhydrous Na₂SO₄ and filtered. After removal of the solvent by rotary evaporation, the residue was purified by column chromatography (silcia) using 5% ethyl acetate/hexane as the eluent to give Compound V (665 mg, 2.25 mmol, 75% yield) as a clear oil. ¹H NMR (500 MHz, CDCl₃) δ 7.39 (dd, J=8.4 Hz, 2.2 Hz, 1H), 7.33 (d, J=2.3 Hz, 1H), 7.14 (d, J=2.2 Hz, 1H), 7.09 (dd, J=8.4 Hz, 2.0 Hz, 1H), 6.91 (d, J=8.4 Hz, 2H), 6.01-5.96 (m, 2H), 5.03-5.11 (m, 4H), 3.86 (s, 3H), 3.78 (s, 3H), 3.43 (d, J=6.5 Hz, 2H), 3.37 (d, J=6.5 Hz, 2H); ¹³C NMR (125 MHz, CDCl₃) δ 156.4, 154.9, 137.8, 137.0, 132.2, 131.0, 130.9, 130.7, 130.5, 128.3, 128.1, 127.9, 115.5, 115.3, 111.3, 109.9, 55.7, 55.4, 39.4, 34.3; IR (film) 3435, 2938, 2836, 1638, 1606, 1493, 1463, 1245, 1134, 1029, 914, 815 cm⁻¹; HRMS (ESI) m/z=295.1698 calcd for C₂₀H₂₃O₂ [M+H]⁺, found 295.1705.

Example 5-1

Honokiol (3',5-diallyl-[1,1'-biphenyl]-2,4'-diol) Using BBr₃-DCM

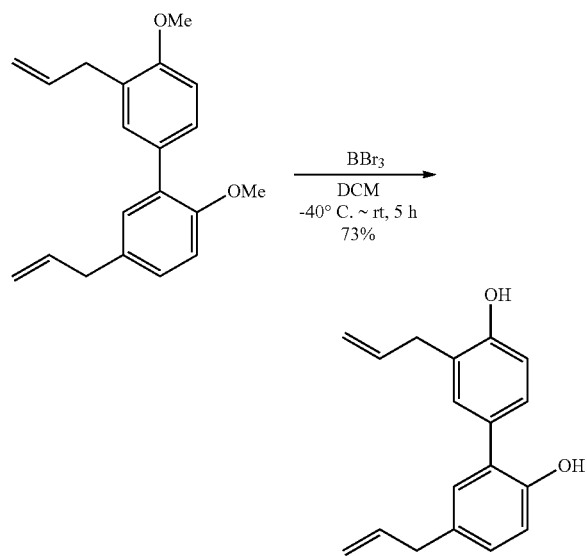

To a solution of Compound V (50 mg, 0.17 mmol) in distilled dichloromethane (1 mL) is added a solution of BBr₃ (0.4 mL, 1 M in dichloromethane) at −40° C. under an argon atmosphere. The resulting mixture is allowed to warm to ambient temperature and is stirred for 5 hours. The reaction is quenched with saturated sodium bicarbonate solution and extracted with dichloromethane (3×10 mL). The combined organic layers are washed with brine (10 mL), dried over Na₂SO₄, and filtered. The solvent is concentrated by rotary evaporation and the residue is purified by column chromatography (silica) with 20% ethyl acetate/hexane as the eluent to give honokiol (32 mg, 0.12 mmol, 73% yield) as a white solid; ¹H NMR (500 MHz, CDCl₃) δ 7.23 (dd, 1H, J=8.0, 2.0 Hz), 7.21 (d, 1H, J=2.1 Hz), 7.05 (dd, 1H, J=8.0, 2.0 Hz), 7.02 (d, 1H, J=2.1 Hz), 6.93 (d, 1H, J=3.8 Hz), 6.90 (d, 1H, J=8.2 Hz), 5.93-6.08 (m, 2H), 5.17-5.24 (m, 3H), 5.03-5.11 (m, 3H) 3.46 (d, 2H, J=6.5 Hz), 3.35 (d, 2H, J=6.7 Hz).

Example 5-2

Honokiol (3',5-diallyl-[1,1'-biphenyl]-2,4'-diol) Using BBr₃-DMS

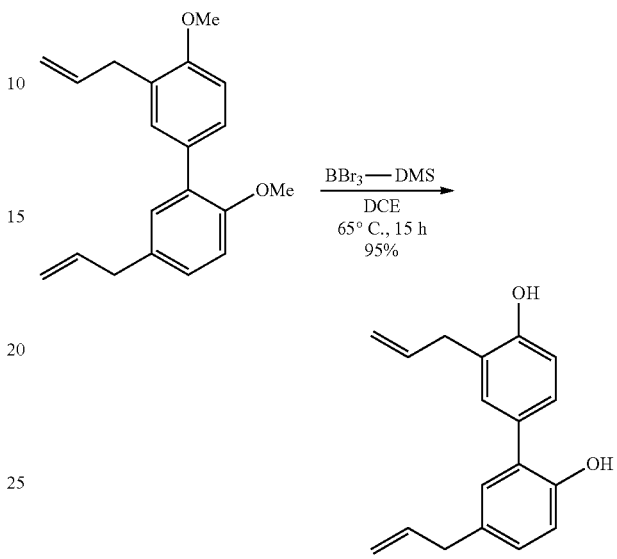

To a solution of Compound V (400 mg, 1.36 mmol) in distilled 1,2-dichloroethane (7 mL) was slowly added BBr₃.DMS complex (1.0 g, 3.26 mmol). The reaction flask was sealed under an argon atmosphere and heated to 65° C. for 15 h. The reaction was quenched with saturated NaHCO₃ solution (15 mL) and extracted with dichloromethane (15 mL×3). The combined organic layers were washed with brine (15 mL), dried over Na₂SO₄, and filtered. The solvent was concentrated by rotary evaporation and the residue was purified by column chromatography (silica) with 20% ethyl acetate/hexane as eluent to give honokiol (345 mg, 1.29 mmol, 95% yield) as a white solid; ¹H NMR (500 MHz, CDCl₃) δ 7.23 (dd, J=8.0 Hz, 2.0 Hz, 1H), 7.21 (d, J=2.1 Hz, 1H), 7.05 (dd, J=8.0 Hz, 2.0 Hz, 1H), 7.02 (d, J=2.1 Hz, 1H), 6.93 (d, J=8.2 Hz, 1H), 6.90 (d, J=8.2 Hz, 1H), 5.93-6.08 (m, 2H), 5.17-5.24 (m, 3H), 5.03-5.11 (m, 3H) 3.46 (d, J=6.5 Hz, 2H), 3.35 (d, J=6.7 Hz, 2H); ¹³C NMR (125 MHz, CDCl₃) δ 153.9, 150.7, 137.8, 136.0, 132.2, 131.1, 130.2, 129.6, 128.8, 128.6, 127.7, 126.4, 116.9, 116.6, 115.6, 115.5, 39.4, 35.1; HRMS (ESI) m/z=265.1229 calcd for C₁₈H₁₇O₂ [M−H]⁻. found 265.1223.

Example 6-1

Compound VI (3,3',5,5'-di-tert-butyl-[1,1'-biphenyl]-2,4'-diol) via AgOAc

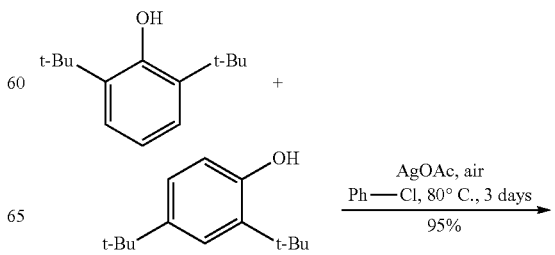

-continued

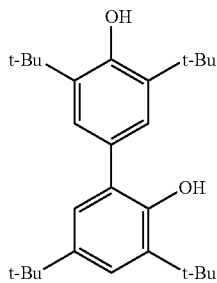

To a 5 mL microwave vial is added a solution of 2,6-di-tert-butyl phenol (20.6 mg, 0.1 mmol) and 2,4-di-tert-butyl phenol (30.9 mg, 0.15 mmol) in 2 mL of chlorobenzene and AgOAc (33 mg, 0.2 mmol). The vial is sealed with a crimping cap and stirred at 80° C. for 3 days. The mixture is then concentrated in vacuo and the residue purified by flash column chromatography on silica gel (hexanes/methylene chloride=30:1 to 10:1) to give Compound VI as a yellow solid (39 mg, 0.095 mmol, 95% yield) $^1$H NMR (500 MHz, CDCl$_3$) 7.34 (d, 1H, J=2.5 Hz), 7.25 (s, 2H), 7.12 (d, 1H, J=2.5 Hz), 5.45 (s, 1H), 5.34 (s, 1H), 1.49 (s, 18H), 1.47 (s, 9H), 1.35 (s, 9H); $^{13}$C NMR (125 MHz, CDCl$_3$) δ 153.79, 149.11, 141.91, 137.10, 135.09, 129.06, 128.64, 126.50, 125.03, 123.44, 35.30, 34.70, 34.51, 31.84, 30.48, 29.89.

Example 6-2

Compound VI (3,3',5,5'-di-tert-butyl-[1,1'-biphenyl]-2,4'-diol) via Cr Catalyst

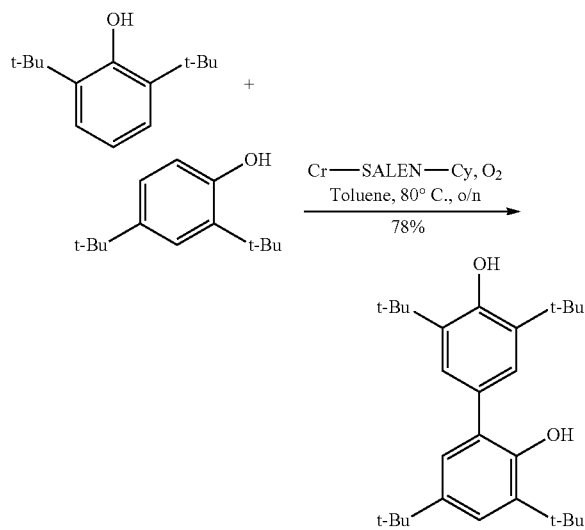

To a 5 mL microwave vial is added a solution of 2,6-di-tert butyl phenol (20.6 mg, 0.1 mmol) and 2,4-di-tert butyl phenol (30.9 mg, 0.15 mmol) in 2 mL of chlorobenzene and Cr-SALEN-Cy catalyst (6.6 mg, 0.01 mmol). Oxygen is added via active purge. The vial is sealed with a crimping cap and stirred at 80° C. overnight. The mixture is then concentrated in vacuo and the residue purified by flash column chromatography on silica gel (hexanes/methylene chloride=30:1 to 10:1) to give Compound VI as a yellow solid (32 mg, 78% yield): $^1$H NMR (500 MHz, CDCl$_3$) δ 7.34 (d, 1H, J=2.5 Hz), 7.25 (s, 2H), 7.12 (d, 1H, J=2.5 Hz), 5.45 (s, 1H), 5.34 (s, 1H), 1.49 (s, 18H), 1.47 (s, 9H), 1.35 (s, 9H); $^{13}$C NMR (125 MHz, CDCl$_3$) δ 153.79, 149.11, 141.91, 137.10, 135.09, 129.06, 128.64, 126.50, 125.03, 123.44, 35.30, 34.70, 34.51, 31.84, 30.48, 29.89.

Example 6-3

Compound VI (3,3',5,5'-di-tert-butyl-[1,1'-biphenyl]-2,4'-diol) via DTBP

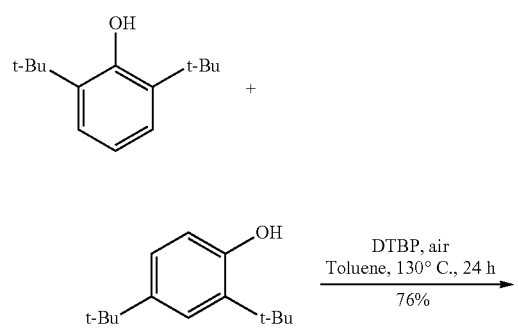

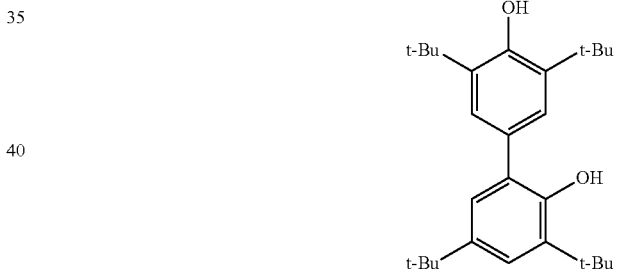

To a 5 mL microwave vial is added a solution of 2,6-di-tert-butyl phenol (103 mg, 0.5 mmol) and 2,4-di-tert-butyl phenol (154 mg, 0.75 mmol) in 2 mL of chlorobenzene and di-tert butyl peroxide (87 mg, 0.6 mmol). The vial is sealed with a crimping cap and stirred at 130° C. After 8 h, additional di-tert butyl peroxide (22 mg, 0.15 mmol) is added to the solution, the vial is resealed, and it is stirred at 130° C. for a further 16 h. The mixture is then concentrated in vacuo and the residue purified by flash column chromatography on silica gel (hexanes/methylene chloride=30:1 to 10:1) to give the Compound VI as a yellow solid (159 mg, 76% Yield): $^1$H NMR (500 MHz, CDCl$_3$) δ 7.34 (d, 1H, J=2.5 Hz), 7.25 (s, 2H), 7.12 (d, 1H, J=2.5 Hz), 5.45 (s, 1H), 5.34 (s, 1H), 1.49 (s, 18H), 1.47 (s, 9H), 1.35 (s, 9H); $^{13}$C NMR (125 MHz, CDCl$_3$) δ 153.79, 149.11, 141.91, 137.10, 135.09, 129.06, 128.64, 126.50, 125.03, 123.44, 35.30, 34.70, 34.51, 31.84, 30.48, 29.89.

Example 7

Compound VII ([1,1'-biphenyl]-2,4'-diol) from Compound VI

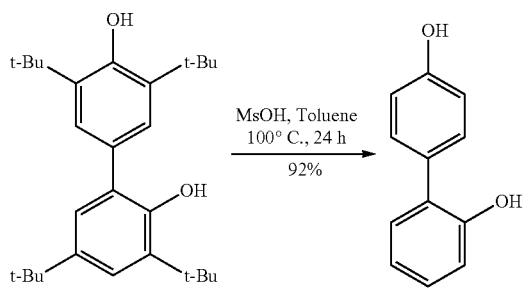 [SMILES: CC(C)(C)c1cc(-c2cc(C(C)(C)C)c(O)c(C(C)(C)C)c2)c(O)c(C(C)(C)C)c1 ; Oc1ccc(-c2ccccc2O)cc1]

To a solution of Compound VI (41 mg, 0.1 mmol) in toluene (2 mL) is added methanesulfonic acid (144 mg, 97 μL, 1.5 mmol) at 100° C. After the starting material is consumed, the reaction is quenched by the addition of water and the mixture is then extracted with EtOAc (50 mL×3). The mixture is concentrated in vacuo and the residue purified by flash column chromatography on silica gel (hexanes/ethyl acetate=10:1 to 6:1) to give Compound VII a yellow solid (17 mg, 92% yield): $^1$H NMR (500 MHz, acetone-d$_6$) δ 8.35 (s, 1H), 8.12 (s, 1H), 7.45-7.41 (m, 2H), 7.25 (dd, 1H, J=7.8, 2.0 Hz), 7.12 (td, 1H, J=7.8, 2.0 Hz), 6.95 (dd, 1H, J=8, 1.0 Hz), 6.91-6.85 (m, 3H).; $^{13}$C NMR (125 MHz, acetone-d$_6$) δ 157.04, 154.71, 131.06, 130.97, 130.61, 129.12, 128.44, 120.59, 116.66, 115.56, 115.47.

Example 8-1

Compound VII ([1,1'-biphenyl]-2,4'-diol) One-Pot via AgOAc

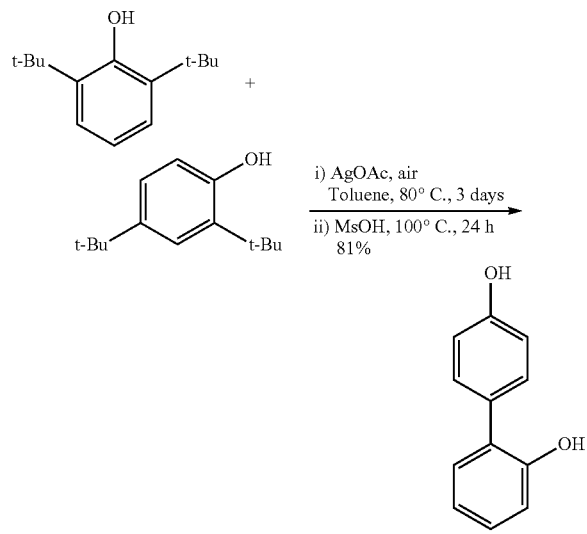

To a 100 mL flask equipped with a reflux condenser is added 2,6-di-tert butyl phenol (2.06 g, 10 mmol), 2,4-di-tert butyl phenol (3.09 g, 15 mmol), AgOAc (3.32 g, 20 mmol) and distilled toluene (50 mL, 0.2 M). The reaction mixture is heated to 90° C. under an oxygen atmosphere for 3 days. The mixture is cooled to ambient temperature. To the resultant solution of 3,3',5,5'-tetra-tert-butyl-[1,1'-biphenyl]-2,4'-diol is added methanesulfonic acid (14.4 g, 150 mmol) slowly over 5 minutes at 0° C., and the solution is heated to 100° C. for 24 h. After stirring at ambient temperature for a further 2 h, the reaction mixture is quenched by addition of 100 mL of deionized water at 0° C. The mixture is thoroughly extracted with EtOAc (3×200 mL). The combined organic layers are concentrated in vacuo and the residue purified by chromatography (silica) using 15% ethyl acetate/hexane as the eluent to afford Compound VII (1.5 g, 8.1 mmol, 81% yield) as a white solid: $^1$H NMR (500 MHz, acetone-d$_6$) δ 8.35 (s, 1H), 8.12 (s, 1H), 7.45-7.41 (m, 2H), 7.25 (dd, 1H, J=7.8, 2.0 Hz), 7.12 (td, 1H, J=7.8, 2.0 Hz), 6.95 (dd, 1H, J=8, 1.0 Hz), 6.91-6.85 (m, 3H); $^{13}$C NMR (125 MHz, acetone-d$_6$) δ 157.04, 154.71, 131.06, 130.97, 130.61, 129.12, 128.44, 120.59, 116.66, 115.56, 115.47.

Example 8-2

Compound VII ([1,1'-biphenyl]-2,4'-diol) One-Pot via Cr Catalyst

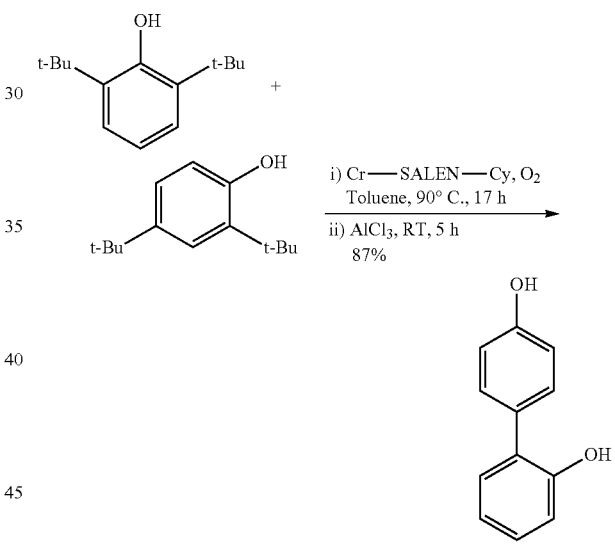

To a 100 mL flask equipped with a reflux condenser is added 2,6-di-tert butyl phenol (3.09 g, 15 mmol), 2,4-di-tert butyl phenol (4.6 g, 22.5 mmol), Cr-SALEN-Cy catalyst (495 mg, 0.75 mmol) and distilled toluene (100 mL, 0.15 M). The reaction mixture is heated to 90° C. under an oxygen atmosphere for 17 h. The mixture is cooled to ambient temperature. To the resultant solution of 3,3',5,5'-tetra-tert-butyl-[1,1'-biphenyl]-2,4'-diol is added aluminium chloride (15.7 g, 120 mmol) slowly over 30 minutes at 0° C., and the mixture is stirred for 5 h at room temperature. The reaction mixture is quenched by addition of 100 mL of deionized water at 0° C. The mixture is thoroughly extracted with EtOAc (3×200 mL). The combined organic layers are concentrated in vacuo and the residue purified by chromatography (silica) using 15% ethyl acetate/hexane as the eluent to afford Compound VII (2.42 g, 13 mmol, 87% yield) as a white solid: $^1$H NMR (500 MHz, acetone-d$_6$) δ 8.35 (s, 1H), 8.12 (s, 1H), 7.45-7.41 (m, 2H), 7.25 (dd, 1H, J=7.8, 2.0 Hz), 7.12 (td, 1H, J=7.8, 2.0 Hz), 6.95 (dd, 1H, J=8, 1.0

Hz), 6.91-6.85 (m, 3H); $^{13}$C NMR (125 MHz, acetone-$d_6$) δ 157.04, 154.71, 131.06, 130.97, 130.61, 129.12, 128.44, 120.59, 116.66, 115.56, 115.47.

Example 8-3

Compound VII ([1,1'-biphenyl]-2,4'-diol) One-Pot via DTBP

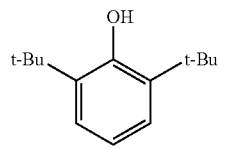

+

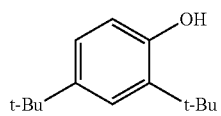

i) DTBP, air
   Toluene, 130° C., 24 h
ii) MsOH, 100° C., 8 h
   88%

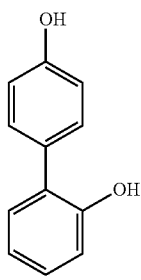

To a 100 mL flask equipped with a reflux condenser is added 2,6-di-tert butyl phenol (2.06 g, 10 mmol), 2,4-di-tert butyl phenol (3.09 g, 15 mmol), di-tert butyl peroxide (2.19 g, 15 mmol) and distilled toluene (50 mL, 0.2 M). The reaction mixture is heated to 130° C. under air atmosphere. After 15 h, additional di-tert-butyl peroxide (2.19 g, 15 mmol) is added, and the mixture is stirred for a further 9 h under air at 130° C. The mixture is cooled to ambient temperature. To the resultant solution of 3,3',5,5'-tetra-tert-butyl-[1,1'-biphenyl]-2,4'-diol is added methanesulfonic acid (14.4 g, 150 mmol) slowly over 5 minutes at 0° C., and the solution is heated to 100° C. for 8 h. After stirring at ambient temperature for a further 2 h, the reaction mixture is quenched by addition of 100 mL of deionized water at 0° C. The mixture is then thoroughly extracted with EtOAc (3×200 mL). The combined organic layers are concentrated in vacuo and the residue is purified by chromatography (silica) using 15% ethyl acetate/hexane as the eluent to afford Compound VII (1.62 g, 8.7 mmol, 88% yield) as a white solid: $^1$H NMR (500 MHz, acetone-$d_6$) δ 8.35 (s, 1H), 8.12 (s, 1H), 7.45-7.41 (m, 2H), 7.25 (dd, 1H, J=7.8, 2.0 Hz), 7.12 (td, 1H, J=7.8, 2.0 Hz), 6.95 (dd, 1H, J=8, 1.0 Hz), 6.91-6.85 (m, 3H); $^{13}$C NMR (125 MHz, acetone-$d_6$) δ 157.04, 154.71, 131.06, 130.97, 130.61, 129.12, 128.44, 120.59, 116.66, 115.56, 115.47.

Example 9

Compound VIII (2,4'-Dimethoxy-1,1'-biphenyl)

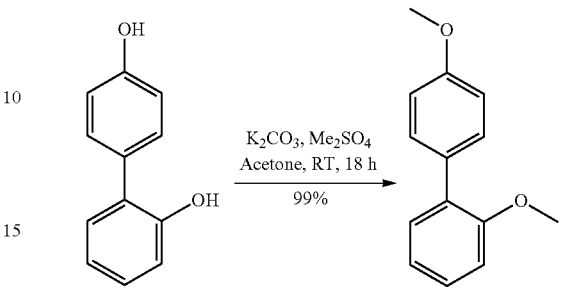

To a stirred solution of Compound VII (1.5 g, 8.1 mmol) in acetone (50 mL, 0.16 M) is added anhydrous potassium carbonate (3.28 g, 24 mmol). After stirring at ambient temperature for 10 minutes, dimethylsulfate (2.54 g, 20.2 mmol) is added and the reaction mixture is stirred for 18 h at ambient temperature. The reaction is quenched with deionized water (50 mL) at ambient temperature and the acetone is removed by rotary evaporation. Ethyl acetate (50 mL) is added and the organic layer is separated, and the aqueous layer is further extracted with EtOAc. The combined organic layers are washed with brine (50 mL) and dried with magnesium sulfate. The residue is concentrated in vacuo to afford Compound VIII as a pale yellow liquid (1.73 g, >99% yield): $^1$H NMR (500 MHz, CDCl$_3$) δ 7.53 (d, 2H, J=9 Hz), 7.38-7.30 (m, 2H), 7.06 (td, 1H, J=7.5 Hz, 1 Hz), 7.03-6.97 (m, 2H), 3.88 (s, 3H), 3.85 (s, 3H); $^{13}$C NMR (125 MHz, CDCl$_3$) δ 158.84, 156.63, 131.08, 130.87, 130.80, 130.50, 128.37, 121.01, 113.68, 111.36, 55.71, 55.44.

Example 10

Compound IX ((3',5-dibromo-2,4'-dimethoxy-1,1'-biphenyl)

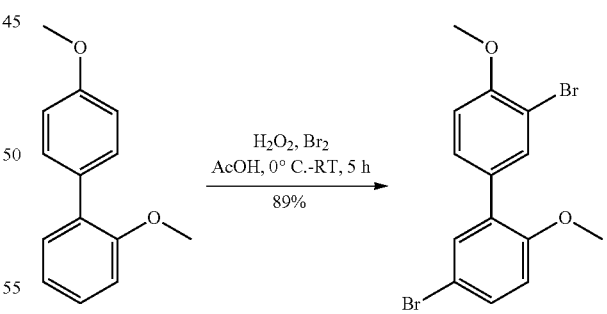

To a stirred solution of Compound VIII (856 mg, 4 mmol) in acetic acid (15 mL, 0.27 M) is added 1 mL of H$_2$O$_2$ solution 30% (w/w) in H$_2$O at 0° C. After stirring at 0° C. for 30 minutes, bromine (752 mg, 4.8 mmol) is slowly added and the reaction mixture is allowed to stir for 4 h at 0° C. After stirring at ambient temperature for a further 1 h, the precipitate is filtered and washed with acetic acid and deionized water. The residue is dried in vacuo to afford Compound IX as a yellowish crystalline solid (1.31 g, 89% yield): $^1$H NMR (500 MHz, CDCl$_3$) δ 7.71 (d, 1H, J=2.0

Hz), 7.43-7.37 (m, 3H), 6.94 (d, 1H, J=8.5 Hz), 6.84 (d, 1H, J=9.5 Hz), 3.93 (s, 3H), 3.80 (s, 3H); $^{13}$C NMR (125 MHz, CDCl$_3$) δ 155.62, 155.31, 134.22, 133.13, 131.26, 130.96, 130.87, 129.62, 113.13, 113.01, 111.53, 111.36, 56.39, 55.94.

Example 11

Compound V (3',5-diallyl-2,4'-dimethoxy-1,1'-biphenyl) from Compound IX

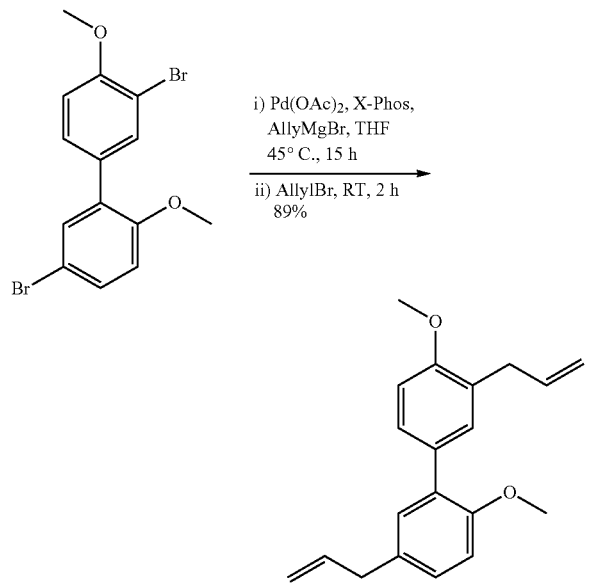

To a stirred solution of Compound IX (1.47 g, 4 mmol) in THF (10 mL, 0.4 M) is added a solution of Pd(OAc)$_2$ (44 mg, 0.2 mmol) and XPhos ligand (95 mg, 0.2 mmol) in THF (5 mL). After stirring for 30 min at ambient temperature, allylmagnesium bromide solution (1.0 M in Et$_2$O, 20 mL, 20 mmol) is slowly added to the mixture and the solution is stirred for 15 h at 40° C. Then allylbromide (2.4 g, 12 mmol) is slowly added at room temperature, and the resulting mixture is stirred for a further 2 h. The reaction is quenched with aqueous NH$_4$Cl (30 mL) and extracted with EtOAc (3×100 mL). The combined organic layers are concentrated in vacuo and the residue is purified by chromatography (silica) using 3% ethyl acetate/hexane as the eluent to afford Compound V (1.06 g, 3.6 mmol, 89% yield) as a colorless liquid; $^1$H NMR (500 MHz, CDCl$_3$) δ 7.39 (dd, J=8.4 Hz, 2.2 Hz, 1H), 7.33 (d, J=2.3 Hz, 1H), 7.14 (d, J=2.2 Hz, 1H), 7.09 (dd, J=8.4 Hz, 2.0 Hz, 1H), 6.91 (d, J=8.4 Hz, 2H), 6.01-5.96 (m, 2H), 5.03-5.11 (m, 4H), 3.86 (s, 3H), 3.78 (s, 3H), 3.43 (d, J=6.5 Hz, 2H), 3.37 (d, J=6.5 Hz, 2H); $^{13}$C NMR (125 MHz, CDCl$_3$) δ 156.4, 154.9, 137.8, 137.0, 132.2, 131.0, 130.9, 130.7, 130.5, 128.3, 128.1, 127.9, 115.5, 115.3, 111.3, 109.9, 55.7, 55.4, 39.4, 34.3; IR (film) 3435, 2938, 2836, 1638, 1606, 1493, 1463, 1245, 1134, 1029, 914, 815 cm$^{-1}$; HRMS (ESI) m/z=295.1698 calcd for C$_{20}$H$_{23}$O$_2$ [M+H]$^+$, found 295.1705.

Example 12-1

Honokiol (3',5-diallyl-[1,1'-biphenyl]-2,4'-diol) Using BBr$_3$-DMS

To a solution of Compound V (1.06 g, 3.6 mmol) in distilled dichloroethane (12 mL) is added a solution of BBr$_3$-DMS (1 M in dichloromethane, 8 mL, 8 mmol) at room temperature under an argon atmosphere. The resulting mixture is stirred for 15 h at 65° C. The reaction is quenched with saturated sodium bicarbonate solution and extracted with dichloromethane (3×100 mL). The combined organic layers are washed with brine (10 mL), dried over Na$_2$SO$_4$, and filtered. The filtrate is concentrated by rotary evaporation and the residue is purified by column chromatography (silica) with 20% ethyl acetate/hexane as the eluent to give honokiol (820 mg, 3.1 mmol, 91% yield) as a white solid; $^1$H NMR (500 MHz, CDCl$_3$) δ 7.23 (dd, J=8.0 Hz, 2.0 Hz, 1H), 7.21 (d, J=2.1 Hz, 1H), 7.05 (dd, J=8.0 Hz, 2.0 Hz, 1H), 7.02 (d, J=2.1 Hz, 1H), 6.93 (d, J=8.2 Hz, 1H), 6.90 (d, J=8.2 Hz, 1H), 5.93-6.08 (m, 2H), 5.17-5.24 (m, 3H), 5.03-5.11 (m, 3H) 3.46 (d, J=6.5 Hz, 2H), 3.35 (d, J=6.7 Hz, 2H); $^{13}$C NMR (125 MHz, CDCl$_3$) δ 153.9, 150.7, 137.8, 136.0, 132.2, 131.1, 130.2, 129.6, 128.8, 128.6, 127.7, 126.4, 116.9, 116.6, 115.6, 115.5, 39.4, 35.1; HRMS (ESI) m/Z=265.1229 calcd for C$_{18}$H$_{17}$O$_2$ [M−H]$^-$, found 265.1223.

Example 12-2

Honokiol (3',5-diallyl-[1,1'-biphenyl]-2,4'-diol) Using BBr$_3$-DMS

To a solution of Compound V (186 mg, 0.63 mmol) in distilled toluene (3 mL) is slowly added BBr$_3$.DMS complex (473 mg, 1.51 mmol). The reaction flask is sealed and heated to 65° C. for 15 h. The reaction is quenched with saturated NaHCO$_3$ solution (7 mL) and extracted with dichloromethane (3×7 mL). The combined organic layers are washed with brine (10 mL), dried over Na$_2$SO$_4$, and filtered. The solvent is concentrated by rotary evaporation and the residue is purified by column chromatography (silica) with 20% ethyl acetate/hexane as eluent to give honokiol (135 mg, 0.57 mmol, 80% yield) as a white solid.

Each patent, patent application, and printed publication, mentioned in this patent document is hereby incorporated by reference in its entirety.

As those skilled in the art will appreciate, numerous changes and modifications may be made to the embodiments described herein, without departing from the spirit of the invention. It is intended that all such variations fall within the scope of the claimed invention.

We claim:
1. A method of making honokiol comprising the reaction of 2-tert-butyl-6-methylphenol with 2-tert-butyl-4-methylphenol to yield 3,3'-di-tert-butyl-5,5'-dimethyl-[1,1'-biphenyl]-2,4'-diol (Compound I):

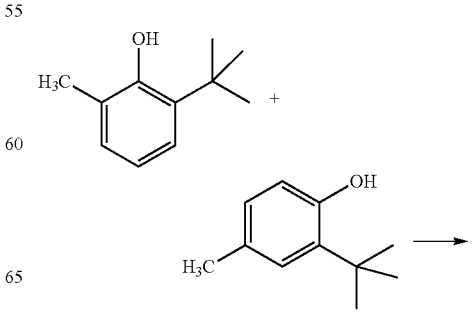

the dealkylation of Compound I to yield Compound II:

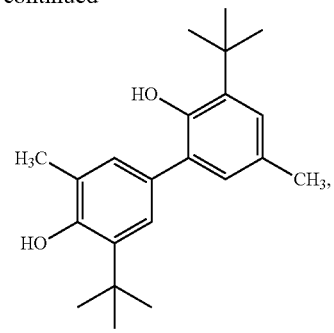

the methylation of Compound II to yield Compound III:

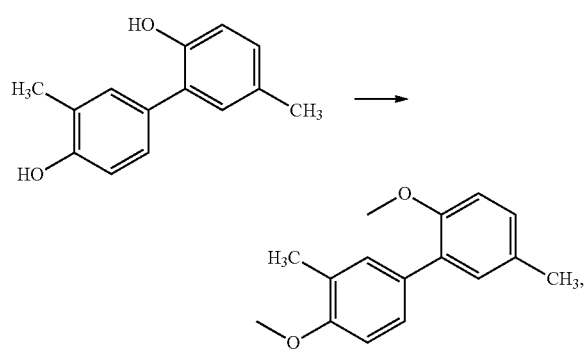

the benzylic halogenation of Compound III to yield Compound IV, wherein X is bromine, chlorine, or iodine:

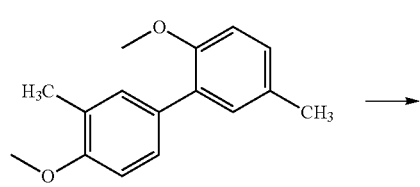

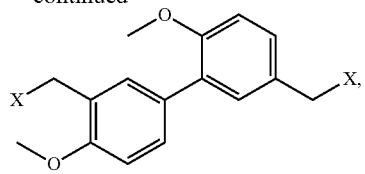

the coupling of a vinylmetallic agent with Compound IV to yield di-allyl compound V:

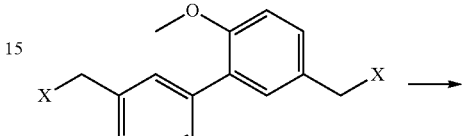

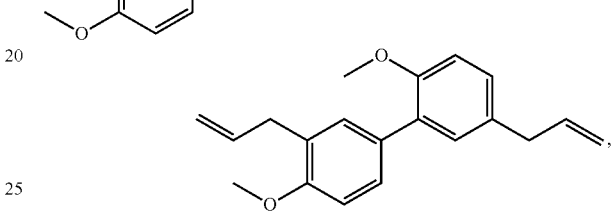

the demethylation of Compound V to yield honokiol:

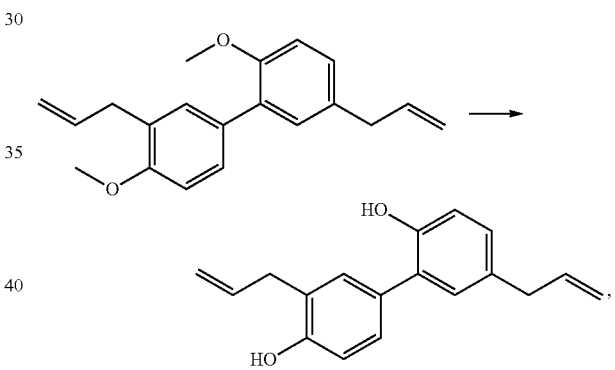

and the isolation of the honokiol from the reaction mixture.

2. The method of claim 1, wherein the reaction comprises the use of a metal catalyst.

3. The method of claim 2, wherein the metal catalyst comprises the metal atom in complex with an acetylacetonate scaffold or an amine or imine scaffold.

4. The method of claim 1, wherein the reaction further comprises an oxidant, optionally, wherein the oxidant is oxygen.

5. The method of claim 1, wherein the cross-coupling reaction and the dealkylation reaction occurs in the same reaction vessel without isolation of the intermediate Compound I.

6. The method of claim 1, wherein the cross-coupling reaction, the dealkylation reaction, and the methylation reaction occurs in the same reaction vessel without isolation of the intermediate Compounds I and II.

7. The method of claim 1, wherein X is bromine.

8. Compound IV, wherein X is selected from bromine, chlorine or iodine.

9. A method of making honokiol comprising the reaction of 2,6-di-tert-butyl-6-phenol with 2,4-di-tert-butyl-4-phenol to yield 3,3',5,5'-tetra-tert-butyl-5,5'-[1,1'-biphenyl]-2,4'-diol (Compound VI):

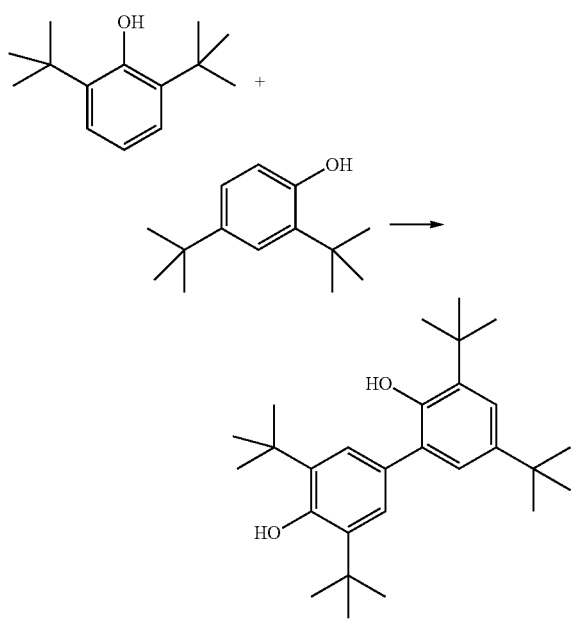

the dealkylation of Compound VI to yield Compound VII:

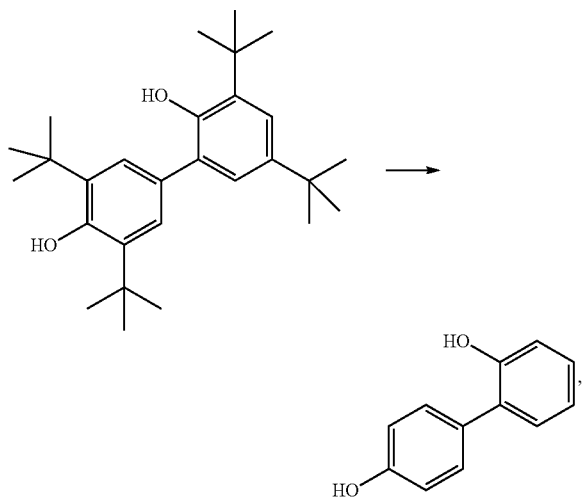

the methylation of Compound VII to yield Compound VIII:

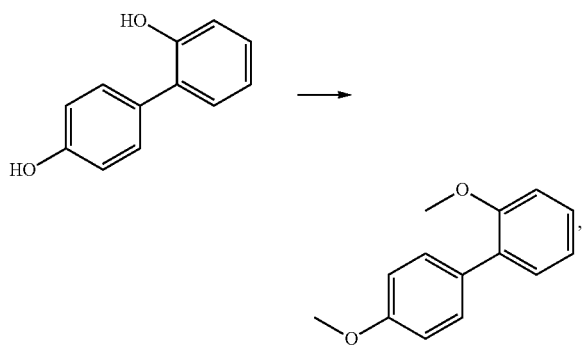

the electrophilic aromatic halogenation of Compound VIII to yield Compound IX, wherein X is bromine, chlorine or iodine:

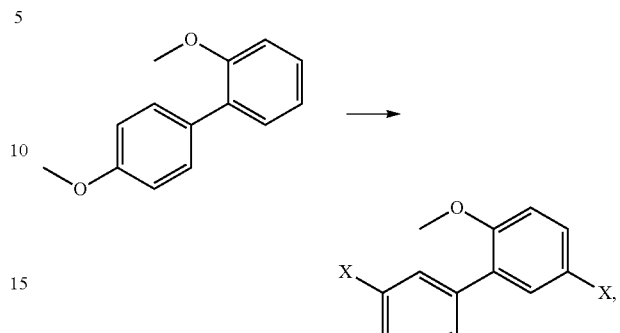

the coupling of an allyl reagent with Compound IX to yield di-allyl compound V:

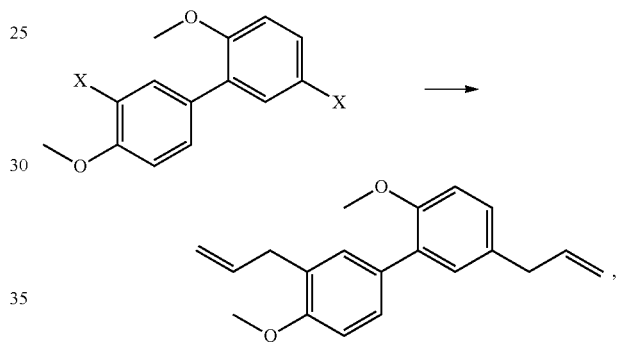

the demethylation of Compound V to yield honokiol, and the isolation of the honokiol from the reaction mixture.

10. The method of claim 9, wherein the reaction comprises the use of a metal catalyst.

11. The method of claim 10, wherein the metal catalyst comprises the metal atom in complex with an acetylacetonate scaffold or an amine or imine scaffold.

12. The method of claim 9, wherein the reaction further comprises an oxidant.

13. The method of claim 12, wherein the reaction further comprises a metal catalyst which is a chromium-Salen complex and wherein the oxidant is oxygen.

14. The method of claim 12, wherein reaction further comprises a solvent which is toluene or chlorobenzene.

15. The method of claim 9, wherein the cross-coupling reaction and the dealkylation reaction occurs in the same reaction vessel without isolation of the intermediate Compound VI.

16. The method of claim 9, wherein the cross-coupling reaction, the dealkylation reaction, and the methylation reaction occurs in the same reaction vessel without isolation of the intermediate Compounds VI and VII.

17. The method of claim 9, wherein X is bromine.

* * * * *